US012555688B1

(12) United States Patent
Cheng et al.

(10) Patent No.: US 12,555,688 B1
(45) **Date of Patent: *Feb. 17, 2026**

(54) DIGITAL TWIN

(71) Applicant: Innovision LLC, Dayton, OH (US)

(72) Inventors: Zhiqing Cheng, Dayton, OH (US); Charles Chen Cheng, Dayton, OH (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/743,321

(22) Filed: Jun. 14, 2024

Related U.S. Application Data

(63) Continuation of application No. 17/751,543, filed on May 23, 2022, now Pat. No. 12,046,374.

(60) Provisional application No. 63/192,054, filed on May 23, 2021.

(51) Int. Cl.

| | |
|---|---|
| ***G16H 50/50*** | (2018.01) |
| ***G16H 10/60*** | (2018.01) |
| ***G16H 20/30*** | (2018.01) |
| ***G16H 30/20*** | (2018.01) |
| ***G16H 50/70*** | (2018.01) |

(52) U.S. Cl.
CPC ............. *G16H 50/50* (2018.01); *G16H 10/60* (2018.01); *G16H 20/30* (2018.01); *G16H 30/20* (2018.01); *G16H 50/70* (2018.01)

(58) Field of Classification Search
CPC ........ G16H 50/50; G16H 20/30; G16H 10/60; G16H 30/20; G16H 50/70
See application file for complete search history.

(56) References Cited

U.S. PATENT DOCUMENTS

| | | | | |
|---|---|---|---|---|
| 8,963,914 | B2 * | 2/2015 | Rawat | G16H 50/20 345/474 |
| 9,727,787 | B2 * | 8/2017 | Wilf | G06V 20/647 |
| 10,220,181 | B2 * | 3/2019 | Giap | A61B 6/03 |
| 10,223,931 | B1 * | 3/2019 | Clark | G09B 19/003 |
| 10,286,179 | B2 * | 5/2019 | Giap | A61B 6/46 |
| 10,293,565 | B1 * | 5/2019 | Tran | A43D 1/02 |
| 10,417,926 | B2 * | 9/2019 | Bachani | A61B 5/0205 |
| 10,430,551 | B2 * | 10/2019 | Wang | G16H 30/20 |
| 11,000,669 | B2 * | 5/2021 | Derungs | A61B 5/0205 |
| 11,051,730 | B2 * | 7/2021 | Tien | G06F 3/011 |
| 11,071,511 | B2 * | 7/2021 | Watanabe | A61B 6/488 |
| 11,093,790 | B2 * | 8/2021 | Chen | G06T 5/70 |
| 11,154,196 | B2 * | 10/2021 | Zhang | G06T 7/33 |
| 11,211,162 | B1 * | 12/2021 | Weiler | G16H 30/40 |
| 11,257,259 | B2 * | 2/2022 | Teixeira | G16H 30/20 |

(Continued)

OTHER PUBLICATIONS

Erol, IEEE, 2020, Sections I-III.*
Liu, Springer, 2021, Chapter 1, Chapter 4.*

*Primary Examiner* — Michael I Ezewoko
(74) *Attorney, Agent, or Firm* — Thomas E. Lees, LLC

(57) ABSTRACT

A patient digital twin platform includes a clinical subsystem, a patient subsystem, and a performance capture system. The clinical subsystem generates physical therapy exercises for a patient. The patient subsystem directs the patient to perform the exercises generated by the clinical patient subsystem. The performance capture system captures measurement data, such as video, of the patient performing at least one physical therapy exercise prescribed by the clinical subsystem. The output of the performance capture system is input to a patient digital twin engine that updates a patient digital twin of the patient.

20 Claims, 11 Drawing Sheets

(56) References Cited

U.S. PATENT DOCUMENTS

| | | | | |
|---|---|---|---|---|
| 11,478,212 | B2 * | 10/2022 | Singh | A61B 5/7267 |
| 11,490,857 | B2 * | 11/2022 | Tien | G16H 20/30 |
| 11,737,832 | B2 * | 8/2023 | Esposito | G02B 27/017 345/156 |
| 11,789,430 | B2 * | 10/2023 | Thomas | G05B 19/4183 700/95 |
| 11,848,095 | B2 * | 12/2023 | Weiler | G16H 20/30 |
| 2004/0002641 | A1 * | 1/2004 | Sjogren | A61N 5/1049 600/407 |
| 2007/0270295 | A1 * | 11/2007 | Balis | A63B 26/00 482/142 |
| 2009/0264796 | A1 * | 10/2009 | Pope | A61B 5/107 600/595 |
| 2010/0111370 | A1 * | 5/2010 | Black | G06F 18/2321 705/26.1 |
| 2013/0345543 | A1 * | 12/2013 | Steibel, Jr. | A61M 21/02 600/407 |
| 2014/0226794 | A1 * | 8/2014 | Quam | A61B 6/06 378/150 |
| 2014/0355735 | A1 * | 12/2014 | Choi | A61B 6/022 378/54 |
| 2015/0154453 | A1 * | 6/2015 | Wilf | G06T 7/564 382/103 |
| 2015/0174362 | A1 * | 6/2015 | Panova | G16H 10/60 600/27 |
| 2015/0213646 | A1 * | 7/2015 | Ma | G06T 7/50 345/420 |
| 2017/0249423 | A1 * | 8/2017 | Wang | G06V 10/7557 |
| 2017/0326332 | A1 * | 11/2017 | Giap | G06T 19/006 |
| 2018/0207484 | A1 * | 7/2018 | Briggs | G16H 40/67 |
| 2018/0228460 | A1 * | 8/2018 | Singh | G01R 33/5608 |
| 2018/0261332 | A1 * | 9/2018 | Baeuerle | G16H 70/60 |
| 2018/0293788 | A1 * | 10/2018 | Black | G06Q 30/0601 |
| 2018/0350144 | A1 * | 12/2018 | Rathod | G06Q 20/3224 |
| 2018/0360313 | A1 * | 12/2018 | Zhang | G06T 7/337 |
| 2019/0005200 | A1 * | 1/2019 | Zimmerman | G16H 50/30 |
| 2019/0030394 | A1 * | 1/2019 | Orr | G16H 20/30 |
| 2019/0057521 | A1 * | 2/2019 | Teixeira | G06V 10/776 |
| 2019/0065970 | A1 * | 2/2019 | Bonutti | G06N 20/00 |
| 2019/0159713 | A1 * | 5/2019 | Kim | A61B 5/742 |
| 2019/0200920 | A1 * | 7/2019 | Tien | A61B 5/0205 |
| 2019/0206134 | A1 * | 7/2019 | Devam | G06F 3/011 |
| 2019/0366030 | A1 * | 12/2019 | Giap | A61B 5/70 |
| 2019/0374741 | A1 * | 12/2019 | Derungs | G06F 3/165 |
| 2020/0126664 | A1 * | 4/2020 | Sato | G16H 50/20 |
| 2022/0015692 | A1 * | 1/2022 | Tien | G16H 20/70 |
| 2023/0136389 | A1 * | 5/2023 | Tien | A61B 5/1486 600/545 |
| 2023/0338095 | A1 * | 10/2023 | Esposito | G16H 30/40 |

* cited by examiner

500

502

500

504

500

506

DIGITAL TWIN

CROSS REFERENCE TO RELATED APPLICATIONS

This application is a continuation of U.S. patent application Ser. No. 17/751,543, filed May 23, 2022, now allowed, which claims the benefit of U.S. Provisional Patent Application Ser. No. 63/192,054, filed May 23, 2021, having the title SCOLIOSIS PATIENT DIGITAL TWIN WITH METHODS AND SYSTEMS FOR ITS CONSTRUCTION AND UTILIZATION, the disclosures of which are hereby incorporated herein by reference.

BACKGROUND

The present disclosure relates to digital twins. More particularly, the present disclosure relates to systems and processes for constructing digital twins, utilizing digital twins, and combinations thereof.

A digital twin is a computer-modeled (virtual) representation of a physical counterpart, such as an object or system. In this regard, the digital twin changes to reflect changes in the physical counterpart. In some applications, a digital twin can span the lifecycle of the physical counterpart. In this regard, the digital twin is periodically updated with data that is collected from, or about the physical counterpart, such that the digital twin models a current state of the physical counterpart.

BRIEF SUMMARY

According to aspects of the present disclosure, a patient digital twin platform comprises a clinical subsystem, a patient subsystem, a performance capture system, and a digital twin evaluation engine. The clinical subsystem prescribes (e.g., generates, curates, creates, customizes, etc.,) physical therapy exercises for a patient. The patient subsystem directs the patient to perform the exercises prescribed by the clinical patient subsystem. The performance capture system captures measurement data of the patient responsive to the patient performing at least one physical therapy exercise prescribed by the clinical subsystem. Here, the exercises are prescribed by the clinical subsystem, but the performance capture system may capture measurement data responsive to exercises directed by the clinical subsystem and/or the patient subsystem. The digital twin evaluation engine updates a digital twin of the patient based at least in part, upon the measurement data from the performance capture system.

According to further aspects of the present disclosure, a process for creating a digital twin is provided. The process comprises selecting a digital twin template that defines parameters that are in common with physical counterparts to be twinned using the selected digital twin template. By way of example, the selected digital template may define a "framework template" that organizes framework parameters of model data associated with a genus, class, group, etc., of physical counterparts to be twinned. For instance, to create a digital twin of a medical patient, the digital twin template may define model data parameters in common with a genus, e.g., humans. Here, the digital twin template may include parameters for a circulatory system, a digestive system, an endocrine system, an integumentary system, an immune system, a muscular system, a nervous system, a renal system, a reproductive system, a respiratory system, a skeletal system, or combinations thereof, etc. For other physical counterparts, a digital twin template can function as a framework template that defines model data parameters that would be common to a genus, class, group, etc., of physical counterparts (e.g., those features that are common to all physical counterparts using the same digital twin template).

The process also comprises instantiating a digital twin from the selected digital twin template. This allows for example, the digital twin template to start being populated with data specific to a physical counterpart. The process also comprises obtaining a first set of input data associated with a first set of parameters defined by the selected digital twin template, where the first set of input data relate to a specific instance of a physical counterpart to be twinned. The process yet further comprises incorporating the first set of input data into the instantiated digital twin.

Still further, the process comprises utilizing coherence relationships to generate a second set of input data, where the second set of input data comprises estimate values for a second set of parameters defined by the selected digital twin template. Here, the coherence relationships utilize the first set of input data to derive the second set of input data. By way of example, by knowing a few parameter values about a counterpart person, e.g., height, weight, age, arm length, leg length, combination thereof, etc., the platform can use this small first set of input data and coherence relationships to derive a large amount of estimate parameter values for the corresponding digital twin, for example, muscle mass, bone density, circulation, lung capacity, etc. Yet further, the process comprises incorporating the second set of input data into the instantiated digital twin.

According to yet further aspects of the present disclosure, a process for using a digital twin is provided. The process comprises utilizing a clinical subsystem to store in a computer platform, prescribed physical therapy exercises for a patient, e.g., a patient with scoliosis. The patient performs exercises under supervised instruction, e.g., in the presence of a clinician, therapist, etc. The process also comprises utilizing a performance capture system to capture baseline measurements (e.g., video) of the patient performing the exercises under the supervised instruction. The process also comprises incorporating the baseline measurements into a digital twin of the patient. Further, the process comprises generating an avatar associated with the digital twin.

The process yet further comprises directing the patient, using a patient subsystem of the computer platform, to perform the exercises generated by the clinical patient subsystem. For instance, the patient may log into the patient subsystem of the computer platform from a remote location, e.g., home. Here, the patient performs the exercises in an unsupervised manner, e.g., not in the presence of the clinician, therapist, etc. By way of example, the process comprises using a simulation of the avatar to graphically display on a graphical user interface, how to perform the exercises. The process also comprises using the performance capture system to capture a set of measurement data (e.g., video) of the patient responsive to the patient performing at least one exercise using the patient subsystem. The process also comprises utilizing the set of measurement data captured by the performance capture system of the patient subsystem to update the digital twin of the patient.

DETAILED DESCRIPTION

Figure 1:
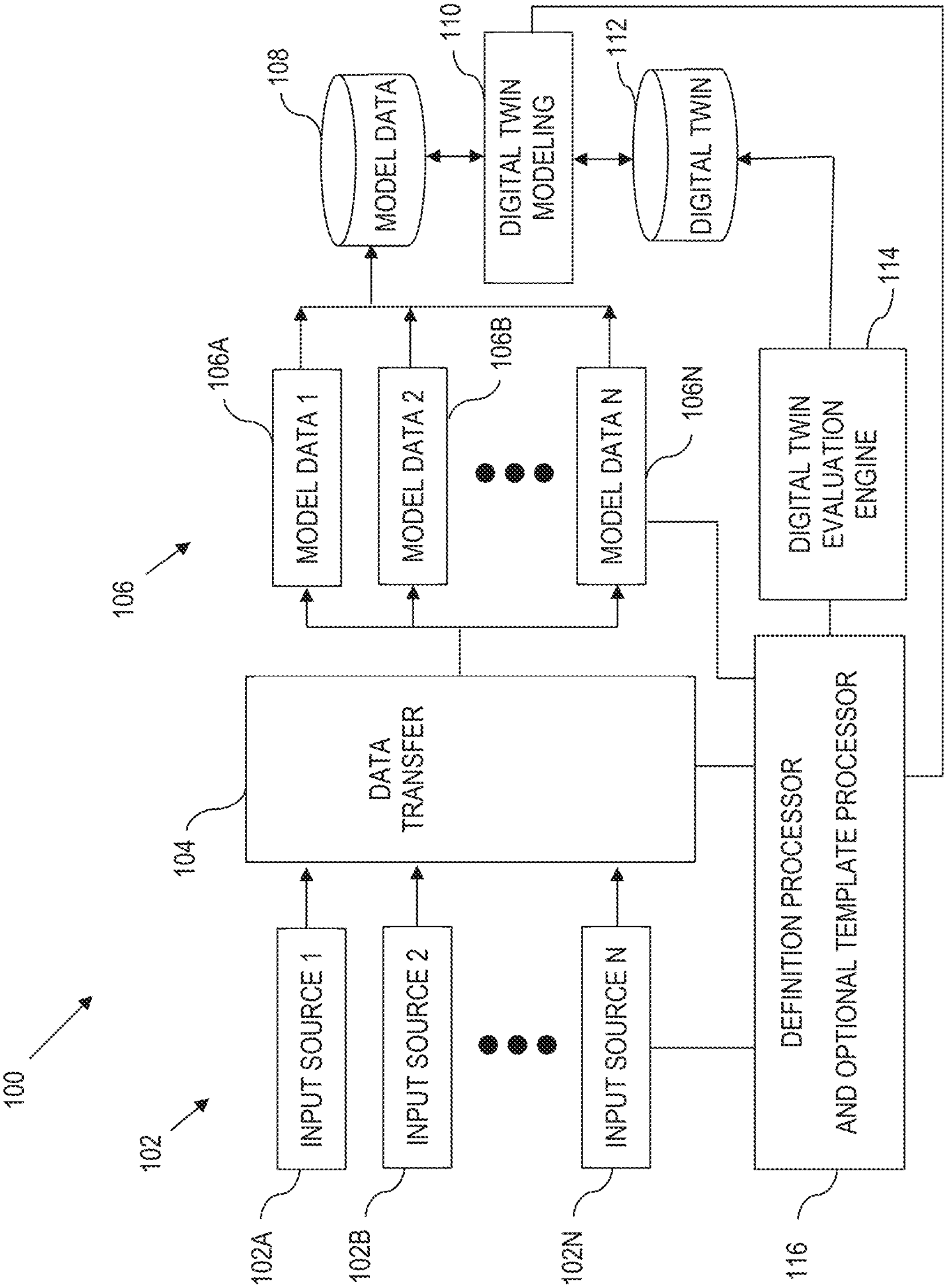
FIG. 1 is an illustration of a digital twin environment, according to aspects herein.

According to various aspects of the present disclosure, systems and processes are provided for constructing a digital twin, utilizing a digital twin, or combinations thereof. In some embodiments, digital twin construction and/or utilization is carried out for medical applications. By way of example, digital twins can be constructed and/or utilized for the evaluation and treatment of patients with medical conditions, patients that suffer from injury, patients having a disease, etc. In a practical application, a digital twin can be utilized in the treatment and care for a patient with scoliosis.

Digital twins can be used in numerous other applications that benefit from, or can otherwise take advantage of a virtualization of a physical counterpart, such as a person, object, system, etc. In this regard, aspects herein can be utilized to construct and use a digital twin corresponding to a physical object or system, which can include humans, other biological entities, structural objects or systems, geological systems, or other objects, particularly those that can change over time. As another example, a digital twin can virtualize abstractions of physical counterparts, e.g., by utilizing a digital twin to represent a population, group or other combination of physical entities/objects that make up the physical counterpart.

A digital twin tightly correlates to a physical counterpart. In this regard, the digital twin herein typically updates and changes in a manner reflective of relevant changes to the physical counterpart. For instance, a digital twin can tightly correlate to an individual, such as by modeling characteristics specific to the individual. In this regard, there may be some parameters that are updated more frequently than others. For instance, a digital twin of an individual may update based upon the weight of the individual once a day, whereas heart rate may be updated with data collected numerous times throughout each day, e.g., potentially in real-time, such by synchronizing a wearable sensor with the platform described herein. Correspondingly, medical records, such as from a physical examination, may only be updated once a year, every six months, or whenever a medical visit is carried out, etc.

A digital twin can also derive one or more characteristics from outside the physical counterpart, such as by utilizing characteristics from a population, segment, system, grouping, etc. By way of example, a digital twin can generally represent an individual, but derive one or more parameters from an abstraction of the individual, e.g., from a group of people such as lineal descendants, from individuals with similar characteristics, from a related class, from a population, from a genus (e.g., humans), etc. Such techniques can be utilized for missing data imputation (e.g., missing data interpolation), for evaluating different scenarios, for training based upon digital twin counterparts, understanding patient trajectories and/or progressions, etc.

In this regard, a digital twin can be characterized as a dynamic digital human model that describes particular/specific aspects of human features or characteristics for an individual, group of people, combination thereof, etc. In the present disclosure, the modeled aspects can vary depending upon needs, the application, the goals of the digital twin, etc.

In certain applications, a digital twin is represented by one or more visual metaphors, such as avatars. In certain applications, a digital twin can be represented by one or more avatars, which use computer graphics to virtually mimic certain human features, such as shape, facial expression, internal features, motion, etc. Additionally, a digital human agent can incorporate human data into particular forms to represent particular attributes or behaviors. Thus, for example, a digital twin can be visualized as a 3-dimensional (3-D) model of the physical counterpart (or relevant aspects thereof). In some embodiments, the avatar (e.g., 3-D model) can be used in simulations, animations, etc., such that the avatar can graphically simulate and display motive activities of the digital twin, thus representing realistic motive activities of the physical counterpart.

In some embodiments, the digital twin technology disclosed herein can be utilized to construct a Scoliosis Patient Digital Twin (SPDT), which is a digital replica (virtual self) of an individual scoliosis patient. As will be described in greater detail herein, the scoliosis patient digital twin is constructed by collecting and processing digital data, which represents personal features, attributes, characteristics, performance, and behavior.

In particular, various aspects of the present disclosure address the technical problem of evaluating physical objects (including persons) that change over time. In particular, aspects herein address the technical problem of evaluating physical objects where actions, activities, or other events that trigger a change in the physical object may not be able to be undone, reversed, or otherwise reset. For instance, a surgery or medical procedure on a person may be permanent; a therapy may cause long lasting results; a treatment for a condition, illness, disease, etc., may have long-term or even permanent consequences. However, such technical problems are addressed by providing a digital twin and platform for utilization thereof. Here, the digital twin can be subjected to changes, e.g., via a simulated surgery, treatment, therapy, change in environment, etc., and the results can be evaluated before subjecting the physical counterpart to any analogous situations/changes. Because the digital twin is a digital representation, the digital twin can be "reset" using prior versions stored in memory, which allows alternative situations to be evaluated on the digital twin, even where the consequences are permanent.

Moreover, because the digital twin is a virtualization, simulations can be run in non-real time, including accelerating time through simulation. This results in the ability to predict future outcomes.

Correspondingly, simulations can be run in real-time, e.g., by implementing graphical animations that display to an output device, e.g., display screen, simulated motive activities of the digital twin, which reflect life-like approximations of corresponding motive activity of the physical counterpart.

Aspects herein also address the technical problem of modifying physical objects where future outcomes may be difficult or impossible to predict. In this regard, aspects herein provide a technical solution that utilizes models that change over time to mimic characteristics of a physical counterpart based upon observational data, measured data, historical data and other sources, as set out in greater detail herein. The models can be tested in various simulation configurations. For example, the models can be utilized to develop and test treatments and therapies and to derive other outcomes that can influence interaction with the physical counterpart.

Still further, aspects herein address the technical problem of accurately and digitally representing therapies, treatments, exercises, required to be performed by an individual where professional supervision may not be available. Here, the solution electronically captures the actual exercises, therapies, treatments, etc., of an individual under clinical and/or professional supervision, e.g., using image capture technology. The captured data is applied to/mapped to a 3-D avatar representing a digital twin of the individual. Here, the captured exercises, therapies, treatments, etc., are carried out virtually by the digital twin in a manner analogous to that of the individual. Thus, the individual can replay the captured data as applied to the digital twin. That is, the individual can view a graphic animation of the digital twin performing in real-time, motive activities, such as stretches, exercises, therapies, treatments, etc., assigned to the individual. This animation is useful, for example, to show/remind/coach/train the individual as to how to keep consistent as the individual practices the stretches, therapies, treatments, exercises, etc., outside the clinical environment/outside the supervision of a professional. In some embodiments, the above animation is extremely customized to the individual because the avatar mimics how the specific individual would/should look when performing the stretches, exercises, therapies, treatments, etc.

The technical solutions herein bring about technical effects including the ability to perform evaluations, predictions, testing, and the ability to explore future outcomes by simulating different exposures, treatments, environments, etc., in a way that does not affect the physical object that has been twinned. Correspondingly, the digital twin is constantly updated based upon real data regarding the physical counterpart, thus maintaining a tight correlation between the physical counterpart and the digital twin. This allows historical data to be captured for the digital twin, and the physical counterpart. As such, initial predictions and simulations can be updated based upon changes to the physical counterpart, and hence the digital twin. Accurate historical accounts of the physical counterpart can be recalled, expanding the ability of a platform. For instance, progressions, trajectories and object pathways can be evaluated based upon retrospection.

Yet further, an avatar can be utilized to represent the digital twin. In this regard, the quality and nature of the avatar can vary. For instance, a representation of the physical counterpart can be implemented as an avatar that is used for reference, visualization, verification, animation, etc. In some embodiments, an avatar represents an accurate depiction of the physical counterpart. Additionally, in some embodiments, the avatar not only reflects characteristics of the physical counterpart, but the digital twin can be "trained" by the physical counterpart, e.g., using image capture, so that range or motion, and other mobility features, capabilities and limitations of the physical counterpart are mimicked by the digital twin, e.g., via animation. Capturing accurate physical characteristics in an avatar creates new and unique opportunities to apply therapies, exercises, stretches, and other physical exertions of the physical counterpart. Such an ability is even more robust where the captured physical characteristics are not static, e.g., where the avatar can mimic motion/movement, speech, balance, gait, flexibility, dexterity, etc., based upon data captured into the digital twin.

The disclosure herein also improves the efficiency of computer systems by fusing together different techniques for creating digital twins, avatars and other visual metaphors, and by constructing evaluation environments as described more fully herein. For instance, by leveraging templates and modeling processes described more fully herein, considerable computing resources are conserved. This scales significantly as the population of digital twins stored on a computer platform grows. Other example efficiencies are described more fully herein.

System Overview

Referring now to the drawings and in particular to FIG. 1, a general diagram of a system 100 is illustrated according to various aspects of the present disclosure. The system 100 is illustrated in block diagram form for constructing and/or using digital twins. In this regard, the system 100 can implement a computer platform that is utilized to construct and/or use digital twins.

The system 100 includes one or more input sources 102 (generally). The illustrated system 100 includes "N" input sources where N is any integer. In particular, the system 100 is illustrated as having input source 102A, 102B through 102N. Each input source 102 represents a source of input data that can be utilized to create a digital twin. As such, each data source 102 will collect, aggregate, or otherwise make available, data that is relevant to the digital twin to be created, updated, maintained, etc. In this regard, the particular application will dictate the nature, type and regularity of data collection and retrieval from each input source 102.

In general, each data source 102 will update over time with new data. The updated data can be specific to a physical object, to a population or group of physical objects, etc. Moreover, the frequency by which each input source 102 generates new data will vary depending upon the nature of the data, the nature of the source, limitations in the technology extracting the data from the source, etc. As such, the system 100 can be configured to receive incoming data as a push, the system 100 can be configured to poll one or more input sources 102, or the system can use a combination of data push and data pull strategies, depending upon the source of the data.

As a non-limiting example, in the context of a digital twin of a human, input source 1 (corresponding to input source 102A) may comprise medical records. Here, the medical records are preferably specific to the individual being digitally twinned. However, there may be benefits to also collecting medical records of individuals with similar characteristics, e.g., to perform missing data imputation (e.g., missing data interpolation), to model alternatives, to test treatment trajectories, etc., as will be described in greater detail herein. In this regard, the input source 102A may in practice, be one or more input sources that pertain to medical records. For instance, the system may be configured to pull medical information from one or more medical repositories in order to obtain a complete set medical records for an individual. Regardless, medical records are typically updated when an individual obtains medical treatment, testing, consultation, etc. As such, the content of the collected data may be highly relevant, but collected periodically, such as yearly, monthly, or whenever medical attention is obtained.

In an analogous manner, the input source 102B may comprise other sources of medical information, such as test reports, lab reports, etc. Again, the input source 102B may in practice, draw from one or more sources, depending upon the availability of data.

As yet another example, input source 102N may be derived from wearable sensors or other periodic data generating information sources. For instance, a fitness tracker, smart phone with health monitoring or fitness tracking, a smart weight scale, a surgically implanted medical device, a body attachable sensor (such as a sensor to measure a voice biomarker, cognitive function biomarker, gait/balance monitor, physical activity monitor, heart rate monitor, body fluid monitor, etc.) can provide input data. In this regard, the input source 102N may again, be a single source, or represent a category of input sources. Notably, the frequency of such data may be daily, or numerous times a day, depending upon the timing of drawing the collected data from the data source 102N. For instance, data from a fitness tracker may be extracted daily, or even several times a day.

Moreover, in some embodiments, any one or more of the input sources 102 may update the system 100 in real-time. For instance, a sensor, e.g., a wearable device may be synchronized to push data to the system 100 in real-time (or near real-time) as the sensor outputs data.

Many other types of input source 102 can be incorporated. Here, the nature of the digital twin, the availability of relevant data and the level of completeness of the digital twin will dictate the number of input sources and how much data is collected.

Data Transfer

Many physical objects, including biological objects, are comprised of complex systems that work together. In this regard, it may be desirable to account for one or more of the individual systems in the construction of a digital twin.

By way of example, a human may be characterized by different anatomical systems (e.g., a circulatory system, a digestive system, an endocrine system, an integumentary system, an immune system, a muscular system, a nervous system, a renal system, a reproductive system, a respiratory system, a skeletal system) some or all of which may be required by a particular digital twin. However, data from the various input sources 102 are not likely to translate into direct values for parameters of the digital twin.

A data transfer mechanism 104 can be provided to sort incoming input data from the various input sources 102 according to systems of interest for the particular digital twin to be constructed. The data transfer mechanism 104 can handle data mapping, transformation, aggregation, manipulation, etc. For instance, the data transfer mechanism 104 can apply rules, machine learning, algorithms, other data processing, combinations thereof, etc., in order to translate available data into meaningful data that enables the digital twin to reflect the physical counterpart.

The system 100 may also include one or more model data mechanisms 106 (generally). Each model data mechanism 106 can represent a container for a particular system, subsystem, or other logical organization of parameters that characterize a digital twin.

For instance, as illustrated, the system 100 includes M model data mechanisms 106 where M is any integer. That is, the system 100 is illustrated as having model data mechanism 106A, model data mechanism 106B . . . model data mechanism 106M. The model data mechanism 106 represent different systems to be characterized by a digital twin. That is, the digital twin can be organized into different models (e.g., muscular system, skeletal system, etc.) This allows an organized way for the data transfer mechanism 104 to distribute relevant data in relevant forms to different systems of the digital twin.

By way of example, in the context of a human digital twin, the data transfer mechanism 104 can transfer incoming data from the input sources 102 into a first model data mechanism 106A representing physical data, a second model data mechanism 106B representing biological data, and a third model data mechanism 106C representing physiological data. Other logical groupings can be implemented, depending upon the nature of the digital twin to be constructed. Thus, there need not be a direct one-to-one correlation between input data from input source(s) 102 and model data mechanism(s) 106. Moreover, one data unit from a particular input source 102 may map to one or more model data mechanisms 106. In this regard, that data unit may take on different formats in different model data mechanisms 106. Yet further, one unit of data need not map directly to a corresponding unit of data generated by a model data mechanism 106. This allows the data transfer mechanism 104 and the model data mechanism 106 to transform input data into meaningful data that can derive, update, modify or otherwise be utilized by the digital twin modeling described more fully herein.

The system 100 also includes a model data storage 108. The model data storage 108 is data storage, e.g., in the form of a database, data source, distributed data sources, data repositories, or other configuration that stores the data generated by the system 100, and in particular, the model data mechanisms 106, as will be described in greater detail herein.

A digital twin modeling engine 110 extracts data from the model data storage 108 and generates digital twins, which are stored in the digital twin model storage 112.

The digital twin model storage 112 is illustrated as separate from the model data storage 108. This is for conceptual purposes. In practice, the digital twin model storage 112 can be comingled or otherwise collocated with the model data storage 108, of the digital twin model storage 112 can be separate from the model data storage 108.

Keeping the digital twin model storage 112 separate from the model data storage 108 enables portability of a digital twin.

A digital twin evaluation engine 114 couples to the digital twin model storage 112. The digital twin evaluation engine 114 enables an end user to inspect, run analysis, run predictions, or otherwise manipulate the digital twin. In this regard, the functions and capability of the digital twin evaluation engine 114 can potentially vary, depending upon the application. That said, certain examples are described in greater detail herein, e.g., with regard to the remaining FIGURES herein.

In some embodiments, an optional definition processor 116 may be provided. The definition processor 116 may communicably couple to one or more components of the system 100. For instance, the definition processor can be coupled to one or more of the input sources 102, the data transfer mechanism 104, the model data mechanisms 106 the digital twin modeling 110, the digital twin evaluation engine 114, combinations thereof, etc.

The definition processor 116, where provided, can be used to set up and define the type of digital twin to be generated, updated and utilized. For instance, the definition processor 116 can be utilized to define the type of digital twin, define the data model mechanisms necessary to generate data for a desired digital twin, define the types of inputs from the input sources 102 required to derive the necessary outputs of the model data mechanism 106, carry out updates, modifications, etc. In some embodiments, the definition processor 116 can also be used to define the transformations, mappings, aggregations, etc., that are implemented by the data transfer mechanism 104. The definition processor 116, the digital twin modeling 110, or a combination thereof can also be used to create a digital twin template model.

Digital Twin Template

Many types of digital twins virtualize complex systems, e.g., human characteristics, anatomy, complex physical objects, etc. In this regard, significant computation power, time, and collected data would be required to generate digital twins from scratch, each time a digital twin is desired. However, a physical counterpart to be twinned is likely comprised of numerous components and systems that are consistent across physical instances, where variation lies in the specific parameters defining the components/systems, etc. By way of example, a genus, group, class, etc., may define common characteristics. As an illustration, medical patients are all from the genus of humans, where all have definable similar traits. For instance, humans have similar skeletal structures. Bone density, bone size, and similar parameters may vary, but the overall skeletal configuration is consistent. As such, the skeletal structure for a human can be templatized. A generic representation of a skeletal structure can be provided as an initial starting point of a framework template. This serves to ensure that the model is complete. This also ensures that necessary and relevant information is collected. In addition to defining relevant parameters for the digital twin, the template can be preloaded with default values. The default values can be derived from similar patient profiles, from historical records, etc. The above-concept can be expanded for all consistent systems. Again, for a human, a nervous system, organ system muscular system etc., can all be templatized and optionally pre-loaded with some or all default values.

As a consequence, the system 100 need only load those data values that differ from the pre-loaded values. This dramatically decreases the time required to create a digital twin. This also reduces the skill and training of the individual setting up the digital twin. A programmer need not fully understand all aspects of the model because the framework is pre-configured by the template and only those dynamic, user-specific variables need to be loaded into the model.

Moreover, in some embodiments, machine learning and computer automated learning is carried out. Since the template defines the key parameters, the digital twin can teach itself to more accurately reflect the physical counterpart by collecting data over time.

Yet further, additional efficiencies are provided, because the input sources 102 can be limited to those necessary to collect dynamic data that changes the state of the physical counterpart. Certain baseline data need not be integrated, where correct values can be integrated into a corresponding digital twin template. In this regard, some templates function as a "framework" template by providing the framework for a set of characteristics (e.g., for a model data mechanism 106).

In this regard, the definition processor 116 can function to provide one or more templates to the digital twin modeling 110. Under this configuration, the digital twin modeling 110 instantiates a digital twin instance from a selected digital twin template, then utilizes information from the model data 108 to adapt the template to reflect the physical counterpart being twinned. That is, the system 100 can instantiate a template model, to create a digital twin instance, then personalize the digital twin instance to derive a digital twin that represents a physical counterpart.

In some embodiments, the above approach can be expanded to include intermediate layers of generalization to expedite the creation and/or updating of a digital twin. The intermediate layers allow flexibility in defining the key constructs of the digital twin. For instance, an intermediate template may be a more complete account of a (potentially optional) subsystem required to model the physical counterpart. By way of example, an intermediate template can be provided for model data mechanism (e.g., a skeletal system, neuromuscular system, etc.). An intermediate template may also optionally include changes that are unique to a specific species. For instance, if the digital twin is a human, a genus template might include basic anatomy, whereas a species template may include specific details unique to a person having a disease, birth condition, injury, etc. This allows rapid characterization and customization.

The above is not limited to humans. The above template and optional intermediate (species) refinement to create a baseline instance can be applied to physical objects, natural phenomenon, etc.

As described more fully herein, the template approach results in a system that provides a functional digital twin upon instantiation. As the digital twin is updated with data that is personalized to the physical counterpart, the confidence in the accuracy of the digital twin increases. Likewise, as data specific to the physical counterpart is used to modify the digital twin, the accuracy of the digital twin increases.

The template-based instantiation of the digital twin provides numerous improvements to the art as noted more fully herein. As a specific example, even if the system does not have access to a complete set of data characterizing the physical counterpart, a digital twin can still be created.

In some embodiments, once the template is instantiated, coherent relationships can be utilized to fill in data fields with personalized data to increase the accuracy of the digital twin. The use of coherent relationships can also significantly reduce the time and resources required to improve the accuracy of the digital twin.

For instance, assume a digital twin is to be created to represent a person. Initially, a template can be used to instantiate the digital twin. Since all humans have certain features, a framework of the digital twin can be readily created that includes a complete set of parameters to be tracked. Moreover, certain parameter values may be pre-populated, which are common to all humans.

Next, a small subset of data can be used to make significant improvements to the accuracy of the digital twin. As an example, the system may input the age, height, weight, arm length, and leg length, combinations thereof, etc., of the physical counterpart. Based upon coherence and a first principles approach, the system makes assumptions and postulates parameters that are used to refine the digital twin. For instance, bone density, bone mass, muscle density, muscle mass, visceral fat, etc., may all be able to be derived from a few parameters. Moreover, knowing generalizations about bone groups, e.g., the length of an arm and/or leg, allows the system to approximate up to an entire skeletal system with estimated values. Thus, a few key measurements from a physical counterpart can automate population of numerous variables/parameters. This intermediate process can utilize an intermediate template, rules engine, a training model approach, or other techniques to apply the updates as described more fully herein.

In addition to the above, the digital twin begins to receive inputs that are used to further refine the representation. For instance, the system can receive X-rays, CT scans, electrocardiogram data, etc. The system can also obtain medical information from electronic medical records that are accessible to the system. As data is collected, the digital twin is refined.

In some embodiments, a full description of the body of the physical counterpart is captured. This facilitates an ability to generate a 3-D model of an individual in an efficient manner.

In some embodiments, the model is further refined by also capturing data descriptive of mobility, gait, balance, speech, and other features that are characteristic of the physical counterpart. All such characteristics are imputed onto the counterpart digital twin.

Training

With a template instantiated, the system 100 can start to train the model(s) to begin mimicking the unique traits and characteristics of the physical counterpart. The confidence levels and accuracy of personalization will increase as unique, specific personalized data is collected. However, by starting with a template, it is possible to create a digital twin, even with incomplete (or even very minimal) personalized data, e.g., because as data is collected over time, the digital twin is refined and more accurately reflects its physical counterpart.

As noted more fully herein, in some embodiments, coherent relationships fill in the necessary data. The use of coherent relationships can persist throughout the model creation and updating. As such, the model data mechanisms 106 can vary in number and purpose, e.g., depending upon how sophisticated the digital twin is, how complete the selected template is, how personalized the digital twin needs to be, etc.

Yet further, in some embodiments, the definition processor 116 can manage a template repository, where one or more templates are selected (and optionally stitched together) to instantiate the starting point/baseline of a digital twin. Here, the definition processor 116 can also be utilized to identify missing/incomplete data, and configure the input sources 102, the data transfer mechanism 104, the model data mechanisms 106, combinations thereof, etc., to "tune" the digital twin modeling 110 to increase the confidence and accuracy of a digital twin over time.

The illustrated system 100 can be comprised of a plurality of hardware processing devices that are linked together by one or more network(s).

In this regard, a process is provided for creating a digital twin, according to aspects herein. The process comprises selecting a digital twin template. For instance, the digital twin template may be a framework template that defines parameters associated with a genus, group, class, etc., of physical counterparts to be twinned. The process also comprises instantiating a digital twin from the selected digital twin template, and obtaining a preliminary set of input data associated with a first set of parameters defined by the digital twin template, where the preliminary set of input data relates to a specific instance of a physical counterpart to be twinned. The process also comprises incorporating the preliminary set of input data into the instantiated digital twin, and utilizing coherence relationships to generate a second set of input data, where the second set of input data comprises estimate values for a second set of parameters defined by the digital twin template, and the coherence relationships are derived from the preliminary set of input data. Also, the process comprises incorporating the second set of input data into the instantiated digital twin.

In some embodiments, selecting the first digital twin template comprises selecting a generic human template that includes anatomical parameters for a digital twin to represent characteristics of a counterpart human. By way of example, obtaining the preliminary set of data may comprise collecting at least one measurement of a physical characteristic of the physical counterpart.

As another example, obtaining the at least one measurement of a physical characteristic comprises a measurement of a length of an arm, a measurement of a length of a leg, a waist measurement, or a combination thereof.

In some embodiments, the process further comprises receiving input data about the physical counterpart that is twinned by the digital twin instance, using a data transfer mechanism to sort the received input data into model data mechanisms, storing an output of the model data mechanisms in a model data storage, and extracting model data from the model data storage to update the instantiated digital twin instance. By way of example, using the data transfer mechanism may further comprise manipulating the received input data into a format that matches at least one parameter of at least one model data mechanism.

Infrastructure

The system 100 can be implemented on a computer system that comprises one or more hardware and/or software processing devices. The processing device(s) can be linked together by one or more networks. Thus, the various components of FIG. 1 need not be co-located. Each network provides communications links between the various processing devices and may be supported by networking components that interconnect the processing devices, including for example, routers, hubs, firewalls, network interfaces, wired or wireless communications links and corresponding interconnections, cellular stations and corresponding cellular conversion technologies (e.g., to convert between cellular and TCP/IP, etc.). Moreover, the network(s) may comprise connections using one or more intranets, extranets, local area networks (LAN), wide area networks (WAN), wireless networks (WiFi), the Internet, including the world wide web, cellular and/or other arrangements for enabling communication between the processing devices, in either real time or otherwise (e.g., via time shifting, batch processing, etc.).

A processing device can be implemented as a server, personal computer, laptop computer, netbook computer, purpose-driven appliance, special purpose computing device and/or other device capable of communicating over the network. Other types of processing devices include for example, personal data assistant (PDA) processors, palm computers, cellular devices including cellular mobile telephones and smart telephones, tablet computers, etc.

Medical Patient Environment

Figure 2:
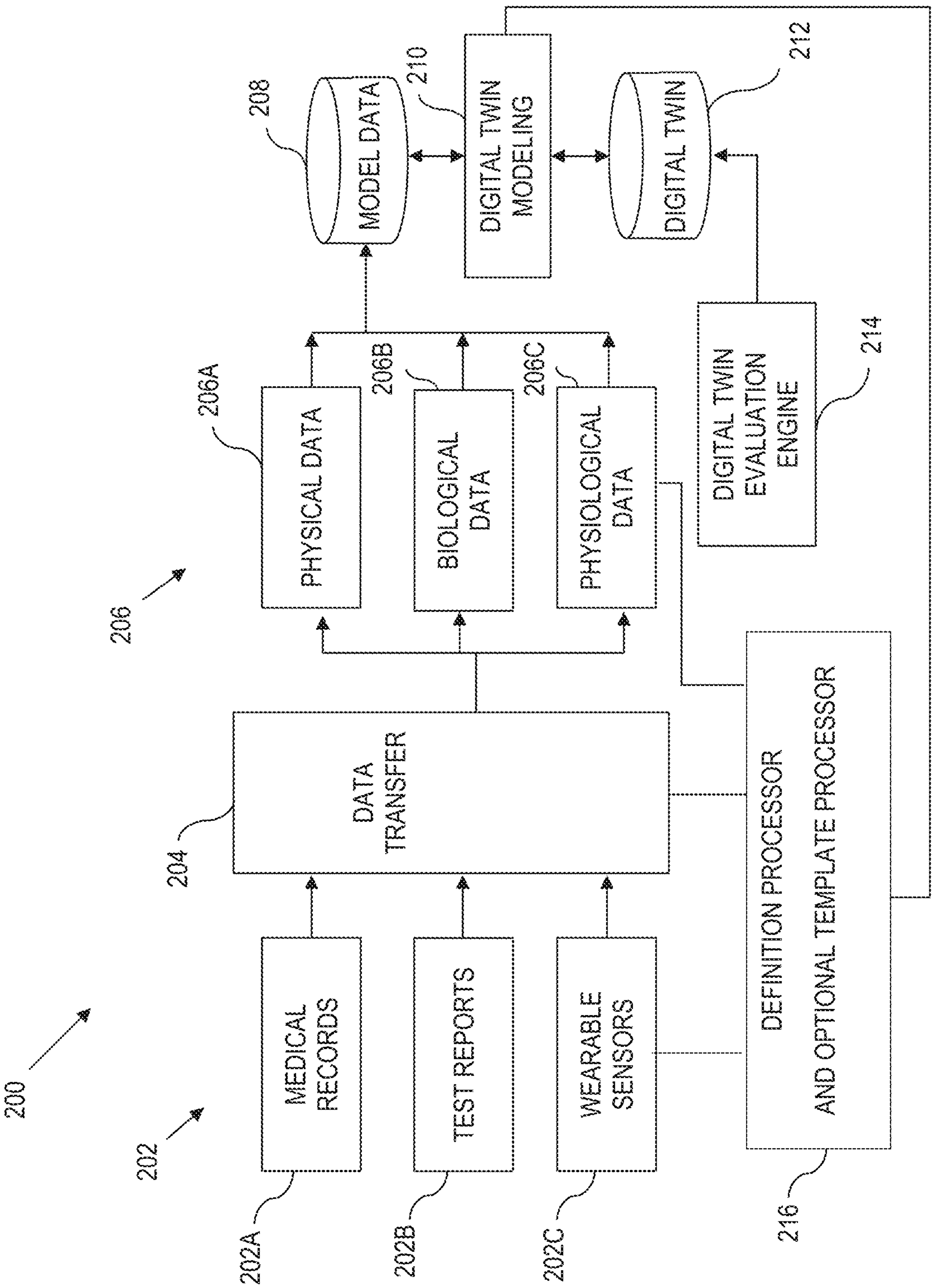
FIG. 2 is an illustration representing an example data collection and management system, according to aspects herein.

Referring to FIG. 2, an example data collection and management system 200 is illustrated, according to aspects herein. The system 200 can include any combination of features described with reference to FIG. 1. As such, like structure is illustrated with like reference numerals 100 higher. In this regard, a practical application of the system 200 does not require all elements shown. Rather, the system 200 is shown for clarity of discussion, and any combination of features may be present. Moreover, the system 200 can implement a computer platform that is utilized to construct and/or use digital twins, as described more fully herein.

The system 100 includes one or more input sources 202 (generally). For instance, as illustrated, the input sources 202 include a medical records input source 202A, a test reports input source 202B, and a wearable sensor input source 202C. Each input source 102 represents a source of input data that can be utilized to create a digital twin of an individual, e.g., a patient. As such, each data source 202 will collect, aggregate, or otherwise make available, data that is relevant to the digital twin to be created. In this regard, the particular application will dictate the nature, type and regularity of data collection and retrieval from each input source 202.

In general, each data source 202 will update over time with new data. The updated data can be specific to the individual being digitally twinned (e.g., personal medical testing and sensor data). Data may also be drawn from a population or group of individuals, such as patients that match a similar patient profile, demographic, location, or other linking characteristic, e.g., to perform missing data imputation (e.g., missing data interpolation), to model alternatives, to test treatment trajectories, etc. Moreover, the frequency by which each input source 202 generates new data will vary depending upon the nature of the data, as noted in greater detail herein.

A data transfer mechanism 204 can be provided to sort incoming input data from the various input sources 202 according to systems of interest for the particular digital twin to be constructed. The data transfer mechanism 204 can handle data mapping, transformation, aggregation, manipulation, etc., as described more fully herein.

The system 200 also includes one or more model data mechanisms 206 (generally). For instance, as illustrated, the system 200 includes a physical data model 206A, a biological data model 206B, and a physiological data model 206C. The model data mechanism 206 represent different systems to be characterized by a digital twin. By way of example, in the context of a human digital twin, the data transfer mechanism 204 can transfer incoming data from the input sources 202 into any anatomical or other logical grouping, as described more fully herein.

The system 200 also includes a model data storage 208. The model data storage 208 is data storage, e.g., in the form of a database, data source, distributed data sources, data repositories, or other configuration that stores the data generated by the system 100, as will be described in greater detail herein.

A digital twin modeling engine 210 extracts data from the model data storage 108 and generates digital twins, which are stored in the digital twin model storage 212.

The digital twin model storage 212 is illustrated as separate from the model data storage 208 for conceptual purposes. In practice, the digital twin model storage 212 can be comingled with the model data storage 208, or the digital twin model storage 212 can be separate from the model data storage 208.

A digital twin evaluation engine 214 couples to the digital twin model storage 212. The digital twin evaluation engine 214 enables an end user to inspect, run analysis, run predictions, or otherwise manipulate the digital twin. In this regard, the functions and capability of the digital twin evaluation engine 214 can potentially vary, depending upon the application. That said, certain examples are described in greater detail herein.

An optional definition processor 216 may also be provided, e.g., to perform system setup, configuration, definition, monitoring, updating, etc., in a manner analogous to that described more fully herein, e.g., with regard to the definition processor 116 (FIG. 1).

Example Scoliosis Patient Digital Twin

In an example embodiment, a scoliosis patient digital twin (SPDT) is a digital replica or representation (virtual self) of an individual scoliosis patient. The scoliosis patient digital twin digitally represents a multitude of features, attributes, characteristics, performance capabilities and/or limitations, behaviors, combinations thereof, etc., of an individual scoliosis patient, and may be based, for example, on personal data and physics/first principles.

In some embodiments, the scoliosis patient digital twin comprises individualized and unified digital models which provide a compact, parameterized representation of an individual scoliosis patient. In some embodiments, the digital models are leveraged by using data containers of personal physical, biological, and physiological data. The scoliosis patient digital twin can be used in scoliosis treatments including physiotherapy, bracing, and surgery. In particular, a hardware-software integrated system can leverage a scoliosis patient digital twin to provide a synthetic, immersive environment for physiotherapists (PTs) and patients to conduct physiotherapy scoliosis specific exercises effectively.

As noted more fully herein, digital twins can be created to represent physical counterparts. For purposes of example application, digital human models can be created, which describe particular aspects of human features or characteristics. Such models may be directed for a group of people, to an individual, or a combination thereof. Additionally, avatars can be constructed, which use computer graphics to virtually mimic certain human features (e.g., a human shape, a facial expression, a range of human motion, etc.). Yet further, human agents can incorporate human data into particular forms to represent particular attributes or behaviors. Yet further, a digital twin can track a lifecycle of portion thereof, with regard to a physics object, system, person, etc.

In an example embodiment, based on physics/first principles, the scoliosis patient digital twin incorporates and utilizes data from, for example, a 3-D body scanner, a motion capture camera, wearable sensors, combinations thereof, etc., to provide real-time, dynamic monitoring, analysis, and synchronized representation of a corresponding physical counterpart, i.e., a real biological human in this example.

Unlike a conventional digital human model that represents a single type of human attribute/characteristics for a group of people or a population, the scoliosis patient digital twin describes and represents body shape, muscular-skeleton (M-S), spine deformity, and body mobility in a unified form for an individual patient. Unlike a computer graphics-based avatar (e. g., one used in computer games) which lacks bio-fidelity and scientific truth, a scoliosis patient digital twin may be based on physics and first principles, thus providing a fidelic and truthful description of an individual patient. Also, unlike a data-driven human agent, which is often in an abstract form, the scoliosis patient digital twin retains and manages the data for a real human.

Aspects herein provide systems, procedures, and methods for the construction of a scoliosis patient digital twin. By way of example, a system may utilize a scoliosis patient digital twin in Physiotherapy Scoliosis Specific Exercises (PSSEs).

Figure 3A:
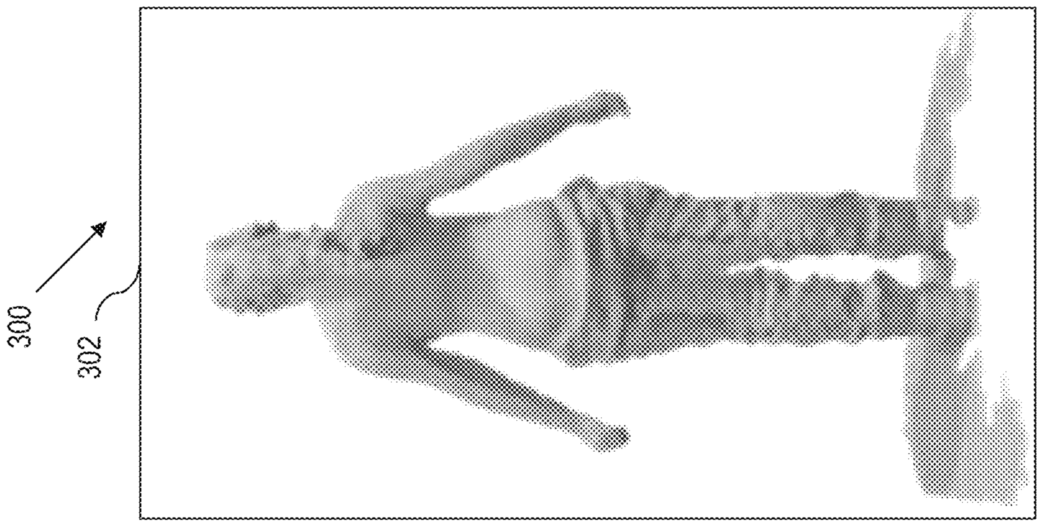
FIG. 3A is an illustration of a shape function of a Scoliosis Patient Digital Twin according to aspects herein.
Figure 3B:
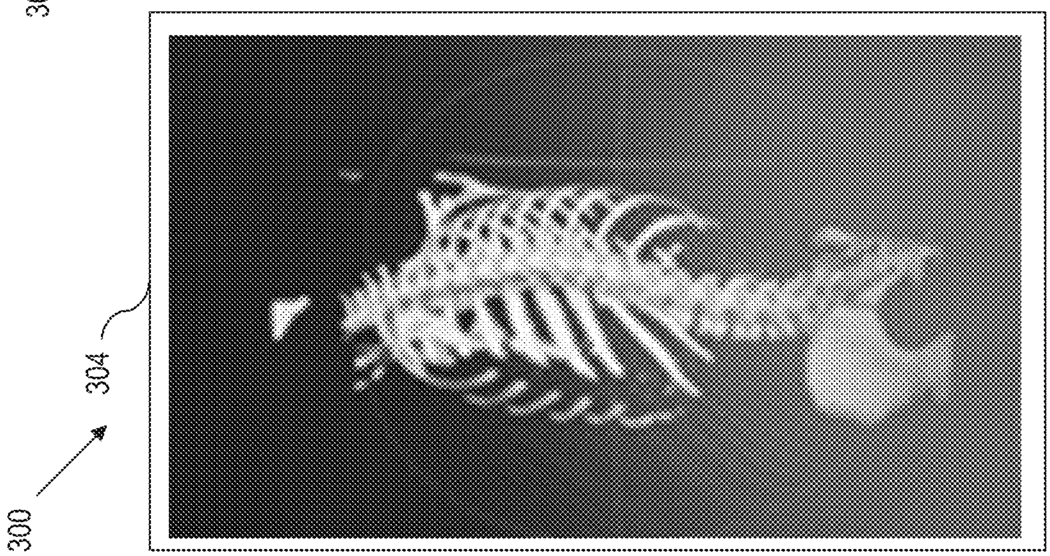
FIG. 3B is an illustration of a skeleton function of a Scoliosis Patient Digital Twin according to aspects herein.
Figure 3C:
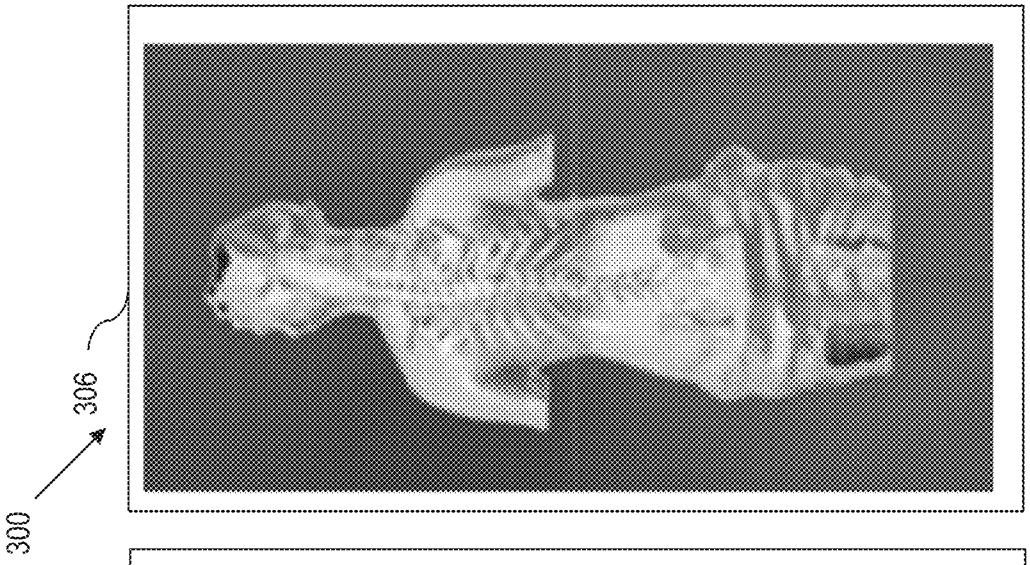
FIG. 3C is an illustration of an integration of shape and skeleton of a Scoliosis Patient Digital Twin according to aspects herein.

Referring to FIG. 3A, FIG. 3B, and 3C generally, aspects herein implement individualized and unified human models combined with personal data containers. In this regard, the models of FIG. 3A, FIG. 3B, and 3C may be implemented as the model data mechanisms 106 (FIG. 1); model data 108 (FIG. 1); digital twin data 112 (FIG. 1); the model data mechanisms 206 (FIG. 2); model data 208 (FIG. 2); digital twin data 212 (FIG. 2), combinations thereof, etc. As such, the discussions of FIG. 1 and FIG. 2 are adopted and usable with the models of FIG. 3A, FIG. 3B, and 3C.

The scoliosis patient digital twin can include but is not limited to the following models and data:

FIG. 3A illustrates a 3-D human body shape model 302 with anthropometry, which provides a complete 3-D surface mesh description of human body shape along with anthropometric measurements, according to aspects herein.

FIG. 3B illustrates a full-body muscular-skeleton (M-S) model 304, which includes bony geometry, rigid linkage with multiple degrees of freedom to define joint kinematics, and Hill-type models of muscles and tendons and provides a non-invasive means to study human kinematics and movement.

FIG. 3C illustrates a full-body anatomy finite element (FE) model 306, which uses solid FE meshes to describe complete anatomical structure of human body in terms of tissue groups.

In practical applications, other models, such as a human behavior model, lifestyle model, cognitive model, etc., can be implemented. Moreover, A in some embodiments, the 3-D human body shape model 302, full-body muscular-skeleton (M-S) model 304, full-body anatomy finite element (FE) model 306, human behavior model, lifestyle model, cognitive model, etc., or combinations thereof, can be implemented as a data model mechanism (106) FIG. 1 and/or a data model mechanism 206 (FIG. 2).

With reference to FIG. 3A, 3B, and 3C generally, data related to the diagnosis and assessment of spine deformity, physiological status, treatment history, and treatment outcomes is collected and is utilized to generate the illustrated models, e.g., using the data collection approaches, e.g., the system 100 of FIG. 1, the system 20 of FIG. 2, or combinations thereof.

Whereas the individualized and unified digital human models are used to represent human anthropometric and biomechanical features and characteristics, data containers are used to store and manage personal physical, biological, and physiological data, health data, activity data, and medical data, and many other types of data.

Scoliosis Patient Digital Twin Construction

Creating a scoliosis patient digital twin (a digital human model) can be a challenge. To keep the effort tractable and affordable, aspects herein use standard models as templates and then create individualized (instance) models from the template models via fitting, morphing, and scaling based on the personal data. As such, the individualized models will provide a sound approximate modeling of the person, with the level of details and fidelity sufficient for intended applications.

Template Model Creation

Figure 4A:
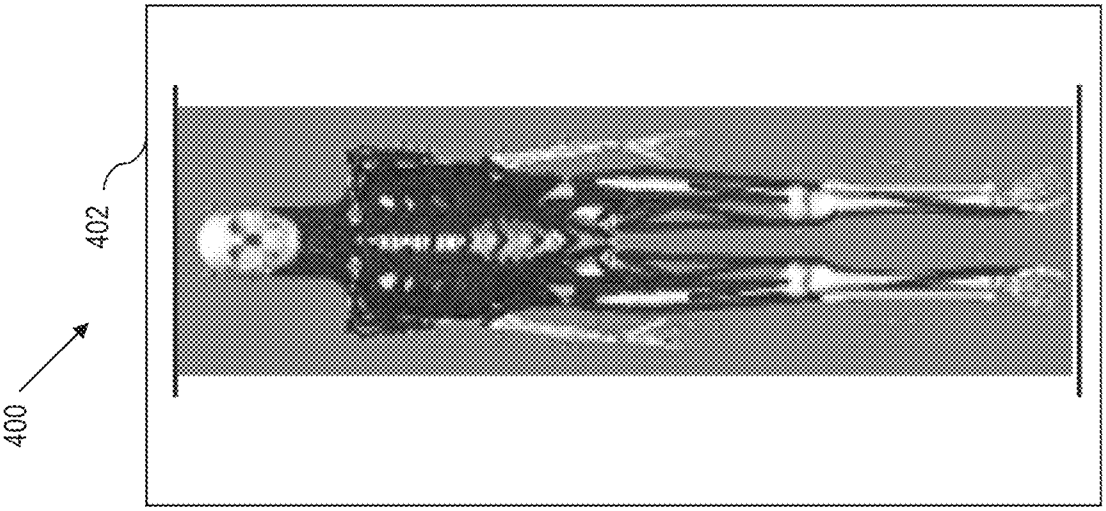
FIG. 4A is an example illustration of a Muscular-skeleton model in a Scoliosis Patient Digital Twin showing a front view, according to aspects herein.
Figure 4B:
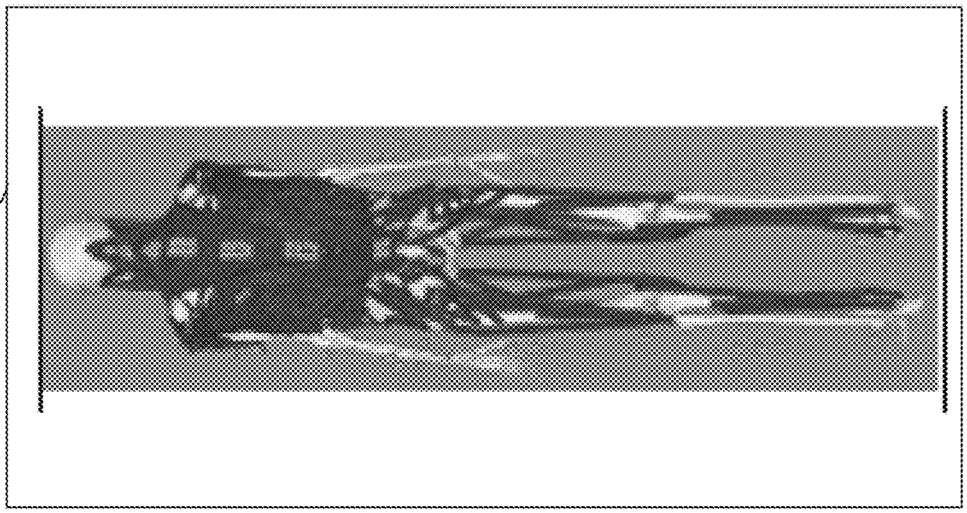
FIG. 4B is an example illustration of a Muscular-skeleton model in a Scoliosis Patient Digital Twin showing a rear view, according to aspects herein.
Figure 4C:
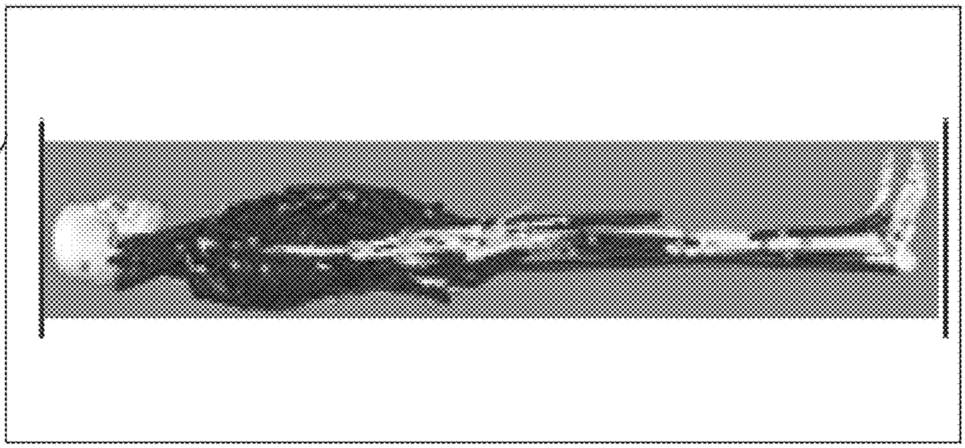
FIG. 4C is an example illustration of a Muscular-skeleton model in a Scoliosis Patient Digital Twin showing a side view, according to aspects herein.

As an example of a scoliosis patient digital twin shown in FIG. 3A, 3B, and 3C, the body shape model (FIG. 3A) can be created from 3-D body scan data using 3D computer graphics software toolset. The body skeleton model (FIG. 3B) can be created from CT scan data using 3D Slicer (3D Slicer is a registered trademark of The Brigham and Women's Hospital, Inc. a Massachusetts Corporation). The integration of the body shape with the skeleton is shown in FIG. 3C. Since physical therapy is intended to recover and strengthen the function of muscles in the back for a body, appropriate modeling and representation of these muscles may be useful. Therefore, the musculoskeletal part of a scoliosis patient digital twin can be enhanced with a biomechanics-based model, an example of which is shown in FIG. 4A, 4B, and 4C. This example model mainly has modeled torso and neck muscles, e.g., modeling 552 muscles. Adjacent vertebral bodies are connected via ball joints that provide three rotational degrees of freedom (flexion/extension, lateral bending, and axial rotation).

Scoliosis Patient Digital Twin Creation Through Individualization

As noted more fully herein, digital twins can be generated though individualization.

Shape Model Creation

In a clinic environment or even at home, a patient's body shape can be captured by for example, an image or video based scanner and then the body shape model can be readily created from depth images. After a shape is derived from 3-D point clouds, the shape can be parameterized by projecting the model in an eigen space composed by principal components of human body shape.

Usually, a scoliosis patient will not be able to withstand a body CT scan. Rather, X-ray images are often taken. Therefore, X-ray images may be utilized to create an instance muscular-skeleton model from its template via the following procedures.

According to further aspects herein, the platform can scale the musculoskeletal model based on attributes of the corresponding physical counterpart, e.g., the subject's height and weight.

Moreover, the platform can adjust the body segment lengths according to a skeleton model provided by the image based scanner. This can be done for example, on a central server.

Skeleton Morphing

Skeleton morphing can be carried out, for example, in the following steps:

Registration

The platform herein (e.g., the digital twin evaluation engine 114; FIG. 2 digital twin evaluation engine 214; FIG. 2) can register X-Ray images (back and side views), which are usually taken for a patient to the body shape model in the coronal plane and sagittal plane, respectively.

Spine Reconstruction

Figure 5A:
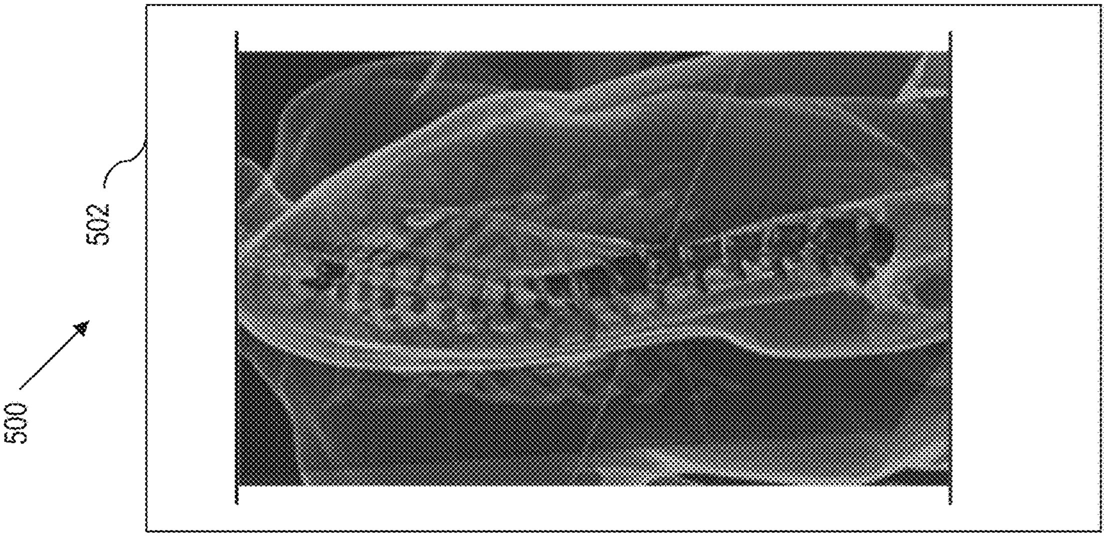
FIG. 5A is an example showing a 3-D spine reconstruction from X-rays and body scan for a scoliosis patient, according to aspects herein.
Figure 5B:
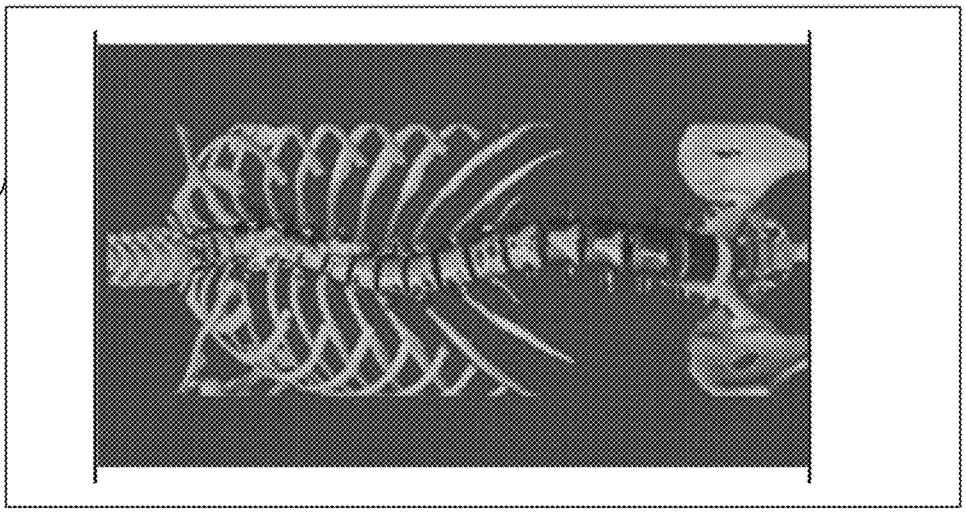
FIG. 5B is an example showing a 3-D spine reconstruction from X-rays and body scan for a scoliosis patient showing X-rays in an A-P plane, according to aspects herein.
Figure 5C:
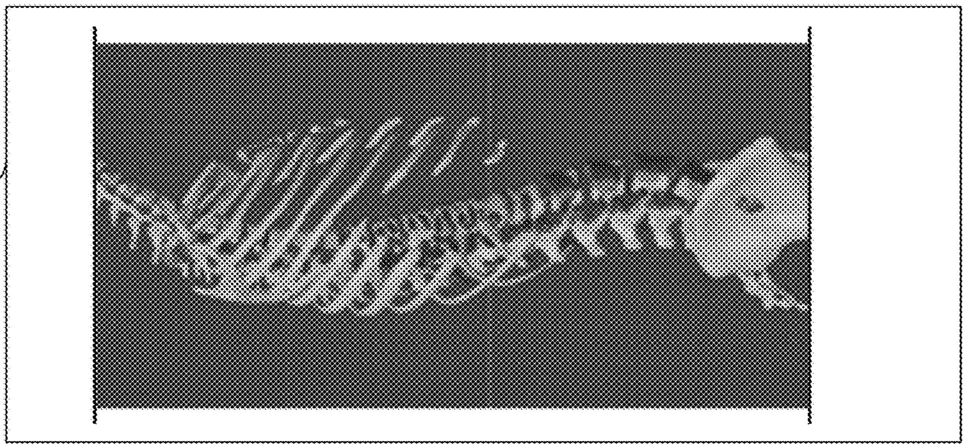
FIG. 5C is an example showing a 3-D spine reconstruction from X-rays and body scan for a scoliosis patient showing X-rays in a lateral plane, according to aspects herein.

The platform herein (e.g., the digital twin evaluation engine 114; FIG. 2 digital twin evaluation engine 214; FIG. 2) can also implement computer code to reconstruct spine column data, e.g., from cl to L5 in 3-D space based on the registered and calibrated X-ray images, with each vertebrate represented by a rigid disk, as shown in FIG. 5A, FIG. 5B, and FIG. 5C. FIG. 5A illustrates a 3-D spine reconstruction 500 from X-rays and a body scan 502 of a scoliosis patient. FIG. 5B illustrates the 3-D spine reconstruction 500 from X-rays and a body scan showing an X-ray 504 in an A-P plane of the scoliosis patient. FIG. 5C illustrates a 3-D spine reconstruction 500 from X-rays and a body scan showing an X-ray in a lateral plane of the scoliosis patient.

Match

Still further, the platform herein can match each vertebrate from a muscular-skeleton template model with a counter vertebrate from a reconstructed patient spine by adjusting vertebrate disk position and orientation.

Morphing

Still further, the platform herein can morph other bone structure of a template muscular-skeleton model accordingly, assuming that a connection between a bone (e.g., rib) and its attached vertebrate is rigid.

Muscle Morphing

Still further, the platform can adjust the muscle groups of a muscular-skeleton template model in length, orientation, attachment, and combinations thereof, based on the skeleton structure of the patient.

As such, the muscular-skeleton model for a patient can be quickly derived from the template muscular-skeleton model to match the physical counterpart actual height, weight, and spine curvature. This model provides a sound approximate modeling of the muscular skeleton and can be used, for example, to define/demonstrate a pose, to replicate a motion, to compute scoliosis curves (Cobb angles), thoracic kyphosis (T4-T12 Cobb angle) and lumbar lordosis (L1-L4 Cobb angle) for an individual patient, combinations thereof, etc.

Integration

Some embodiments can further integrate a shape model and a muscular-skeleton model to become a full body model by associating the body surface vertices with its underlying bone structure. As such, realistic body deformation can be attained when the entire body is articulated. The integrated model may constitute a main part of a scoliosis patient digital twin. In addition, the platform herein can use data containers (e.g., see model data mechanisms 106, model data 108, digital twin data 112; FIG. 1 and/or model data mechanisms 206, model data 208, digital twin data 212; FIG. 2) to hold other physical and physiological data, pose data, motion capture data, and other medical information.

Data Collection and Management

Some patient features or status are not suitable to be represented by a model or need to be updated frequently or monitored in real-time. Therefore, in reference back to FIG. 1, FIG. 2, or combinations thereof, a scoliosis patient digital twin data management system (e.g., see input sources 102, data transfer 104, definition processor 116; FIG. 1 and/or input sources 202, data transfer 204, definition processor 216; FIG. 2, for example) can be created to:

(a) collect data form various sources which include but are not limited to personal medical records, personal medical test reports, and wearable sensors put on an individual;

(b) transfer the data into respective data containers; and (c) store and manage the data with a data server.

The personal data associated with a scoliosis patient digital twin can be categorized in terms of, for example, (a) physical, biological, and physiological feature/characteristics;

(b) static or dynamic;

(c) discrete or continuous (sequential);

(d) 1-D, 2-D, or 3-D; and (e) images, signals, digital records, and text records.

The System for Scoliosis Patient Digital Twin Utilization

The scoliosis patient digital twin created according to aspects herein, is based on personal data and physics first principles. Aspects herein can be utilized in scoliosis treatments including physiotherapy, bracing, and surgery. In particular, a hardware-software integrated system provides a synthetic, immersive environment for physiotherapists (PTs) and patients to conduct physiotherapeutic scoliosis-specific exercises (PSSEs) effectively.

Figure 6:
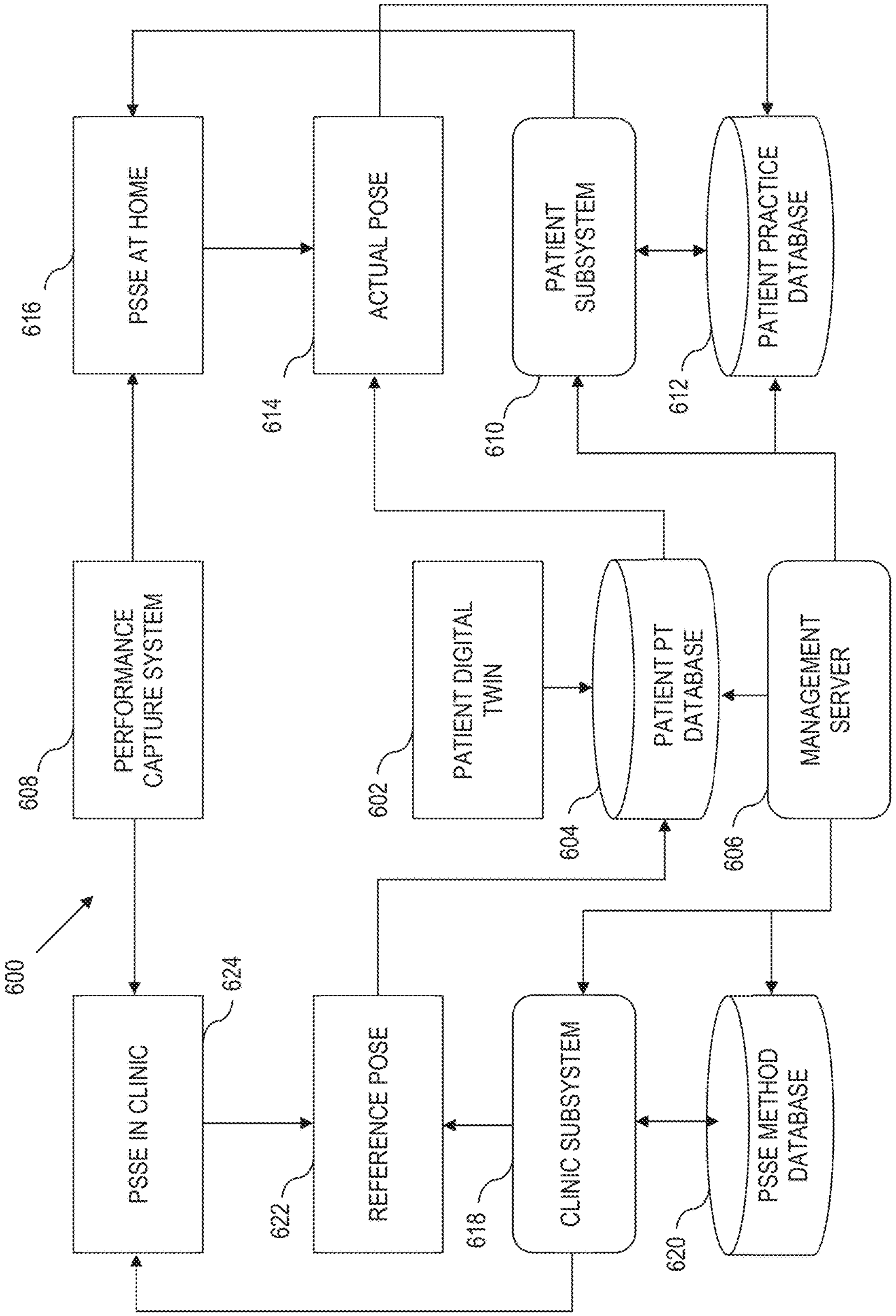
FIG. 6 is an example illustration of an overview of an exercise platform, according to aspects herein.

Referring to FIG. 6, a platform 600 uniquely integrates cutting edge technologies of computer vision, extended reality, serious games, and can leverage various therapies, e.g., Sono and Photodynamic Therapy. The platform 600 is particularly well suited for those treating individuals with scoliosis.

For instance, the platform 600 can utilize a generated scoliosis patient digital twin 602, which serves as a digital or virtual representation describing a body shape and muscular-skeletal structure of a patient. In some embodiments, the scoliosis patient digital twin 602 can optionally be created using the system 100 (FIG. 1) or the system 200 (FIG. 2).

Moreover, in some embodiments, the scoliosis patient digital twin 602 further contains diagnosis and other medical information of the patient.

The scoliosis patient digital twin 602 is stored in a patient database 604, which also stores updated versions of the scoliosis patient digital twin 602, as well as physiotherapeutic scoliosis-specific exercises for the patient.

The patient database 604 is accessed by a management server 606, which handles access to the patient, including accessing the scoliosis patient digital twin 602 and physiotherapeutic scoliosis-specific exercises for the patient. As will be described in greater detail herein, the management server is also configured to handle clinical and patient registration, tele-remote health access, privacy, security and other relevant management functions.

The platform 600 also includes performance capture system 608. As an example of a practical application, a performance capture system can use a measurement device, e.g., a capture camera or other suitable sensor technology, e.g., Microsoft Azure Kinect, to capture body shape, to identify body pose, to track body motion during exercise, to allow the patient to interact with the system via voice commands, combinations thereof, etc. In some embodiments, reference to a performance capture system 608 could include multiple measurement devices, e.g., cameras, that are not co-located. This allows clinical visits and home exercises to each use a measurement device, e.g., camera, within the definition of a performance capture system.

The platform 600 further includes a patient subsystem 610 that is communicably coupled to the management server 606. The patient subsystem 610 performs patient-centric functions, such as physiotherapeutic scoliosis-specific exercise management, practice and capture using the performance capture system 608, monitoring and assessment of the patient, etc. For instance, the patient subsystem 610 can handle model creation, data acquisition and processing, computer vision, and performance evaluation. In this regard, the patient subsystem 610 allows a physical therapist to plan and design physiotherapeutic scoliosis-specific exercises for a patient. Moreover, the patient subsystem 610 guides a patient to perform an exercise according to requirements and to track the progress interactively.

By way of example, the patient subsystem 610 can access a patient practice database 612, which can be utilized to store practice/exercise historical records.

The platform can capture the actual pose 614 of the patient as the patient is performing an exercise. This can be accomplished for instance, based upon the management server 606 controlling the performance capture system 608 to record an actual exercise of the patient. The results are stored in the patent practice database 612 via the patient subsystem 610.

In some embodiments, the platform 600 supports home-based exercise 616. In this regard, a smart television, computer, tablet, smart phone or other suitable device can be utilized to provide guided instruction to the patient to perform the exercise.

To support the exercises, the platform can include a clinical subsystem 618 that is communicably coupled to the management server 606. The clinical subsystem 618 can process diagnosis and assessment data, handle physiotherapeutic scoliosis-specific exercises management, train a patient to perform a physiotherapeutic scoliosis-specific exercise, and capture a patient's motion. For instance, the clinical subsystem 618 can access and store such data in a physiotherapeutic scoliosis-specific exercise method database 620.

The clinical subsystem 618 can be utilized to provide reference poses and exercises 622 as well as facilitate physiotherapeutic scoliosis-specific exercises in a clinical environment, e.g., using the performance capture system 608 to capture the interaction of a therapist with the patient.

In this regard, the platform 600 can leverage rich graphical environments to capture measurements, e.g., video for subsequent storage, analysis, and to update the digital twin 602. The graphical environment can be utilized to display video so that the patient and/or therapist can view exercise reference poses and compare the reference with the actual pose. Moreover, the platform 600 can provide data remotely, e.g., for telehealth, such as for doctors to review patient data remotely, and to assist patients remotely, e.g., so that patients can perform therapy at home or at other remote locations.

Example Digital Twin System

Figure 7:
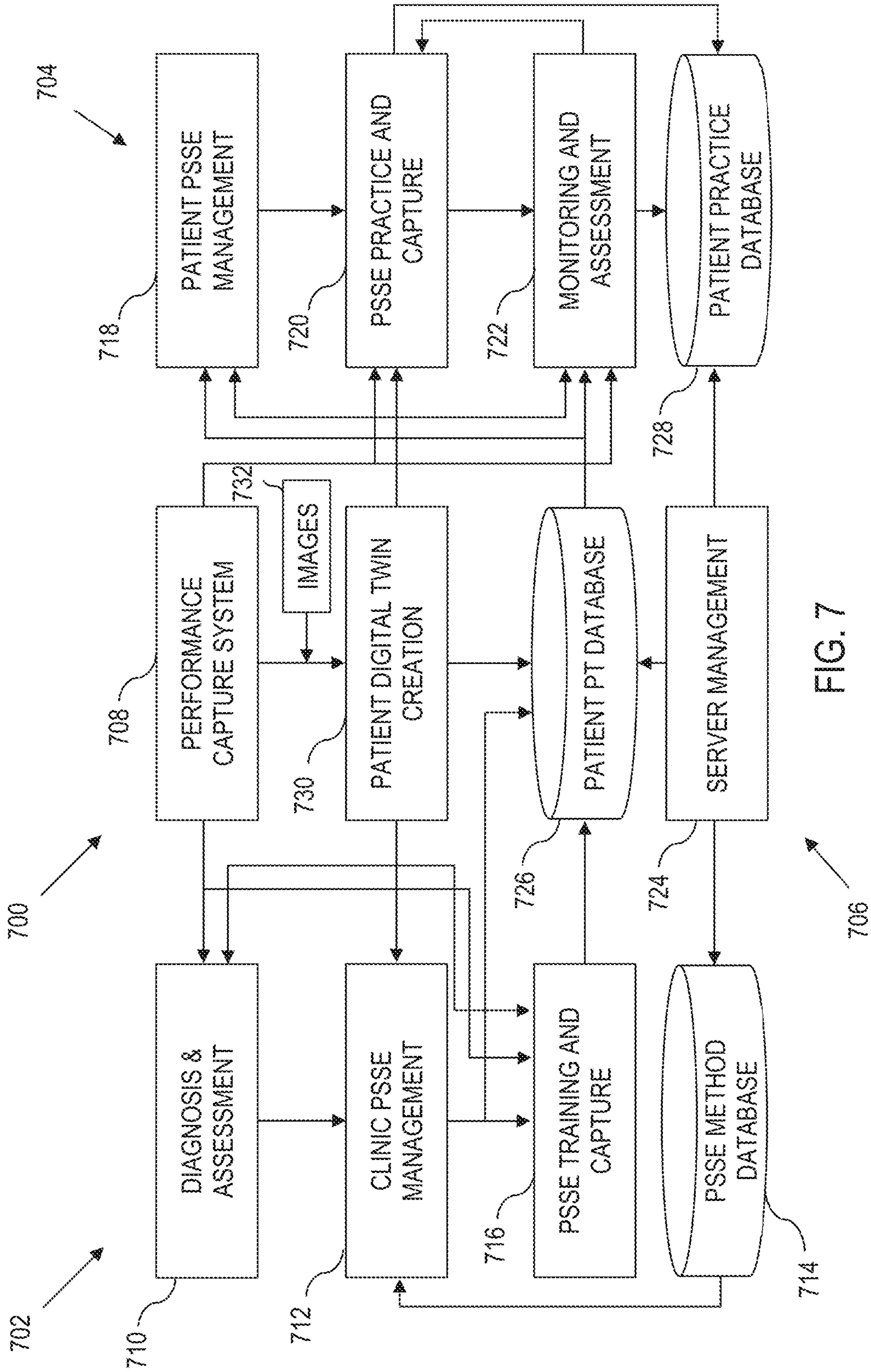
FIG. 7 is an example of a software framework with subsystems and databases according to aspects herein.

Referring to FIG. 7, an example is provided of a platform 700 for providing interactions with a digital twin. The platform 700 can be used to implement the platform 600, and thus the platform 700 can implement or otherwise utilize any combination of features described with reference to FIG. 1-FIG. 6. The platform 700 includes generally, three subsystems, including a clinical subsystem 702, a patient subsystem 704, and a management subsystem 706. The platform 700 also includes a performance capture system 708, which is analogous to the performance capture system 608 described with reference to FIG. 6.

Clinic Subsystem

The clinical subsystem 702 can be architected to be useful, even for a small clinic with a solo or a few physical therapists. Moreover, the clinical subsystem 702 can be based on a normal physiotherapy (PT) workflow. In this regard, the clinical subsystem 702 can be implemented as a windows-based program for either a laptop computer or a desktop computer, connected to a cloud server. The clinical subsystem 702 can utilize a user interface for the user to use the performance capture system 708 in a clinic setting. Moreover, the illustrated clinical subsystem contains three modules, discussed below.

A diagnosis and assessment module 710 helps the care provider to make an accurate diagnosis and assessment of a patient before starting a physical therapy treatment. The diagnosis and assessment module 710 provides functions for observation and classification of scoliosis, for example, based on Rigo classification, calculating Cobb angle, identifying landmarks, and determining kinematics (e.g., pose and motion analysis). The diagnosis and assessment module 710 can further utilize the data captured by performance capture system 708 and can utilize a scoliosis patient digital twin created for the patient. Moreover, the diagnosis and assessment module 710 provides the data and information required for the planning and design of physical therapy for the patient.

A clinic physiotherapeutic scoliosis-specific exercise management module 712 is utilized for selection, customization, and planning of exercises for a patient. In a practical application, the clinic physiotherapeutic scoliosis-specific exercise management module 712 includes user interface (UI) for the care provider to make a physical therapy plan for the patient by selecting appropriate physiotherapeutic scoliosis-specific exercises from a physiotherapeutic scoliosis-specific exercise method database 714. The clinic physiotherapeutic scoliosis-specific exercise management module 712 can also perform customizing physiotherapeutic scoliosis-specific exercises according to unique features and situations of the patient, where the scoliosis patient digital twin will be used as a 3-D reference. In some embodiments, the requirements of each physiotherapeutic scoliosis-specific exercise and performance metrics will be defined via clinic physiotherapeutic scoliosis-specific exercise management module 712.

The scoliosis-specific exercise method database 714 stores physiotherapeutic scoliosis-specific exercise information, e.g., exercises based upon Schroth, Scientific Exercises Approach to Scoliosis (SEAS), etc.

A physiotherapeutic scoliosis-specific exercise training and capture module 716 provides pose and motion demonstrations and can optionally provide therapeutic games. For instance, in a clinic environment, part of a treatment may include training the patient to do a physiotherapeutic scoliosis-specific exercises according to specifications and requirements. The training process of a physiotherapeutic scoliosis-specific exercise can, for instance, be captured and then further converted to a game, which can then be used as instruction material to provide 3-D visual guidance to the patient in order to attain designated pose/motion at home.

Patient Subsystem

The patient subsystem 704 is created for an individual scoliosis patient to do physiotherapeutic scoliosis-specific exercises at home. The patient subsystem 704 can be run on a smart television, computer, laptop, tablet or smartphone. For instance, the patient subsystem 704 can be designed as a mobile app connected to a cloud sever, to allow the user (an individual patient) to handle all tasks related to physiotherapeutic scoliosis-specific exercises at home from a smart phone. The illustrated patient subsystem 704 contains three modules, described below.

A patient physiotherapeutic scoliosis-specific exercise management module 718 allows a patient to plan and manage physiotherapeutic scoliosis-specific exercises at home. The patient physiotherapeutic scoliosis-specific exercise management module 718 generates a user interface with menu options that are navigable by the scoliosis patient. The patient physiotherapeutic scoliosis-specific exercise management module 718 also allows the use to select image/video and music to create a joyful, pleasant virtual environment.

A physiotherapeutic scoliosis-specific exercise practice and capture module 720 can handle the input/output needs of the patient subsystem 704. For instance, in a practical application, the physiotherapeutic scoliosis-specific exercise practice and capture module 720 utilizes at least one input device, e.g., a microphone, voice recognition capability, etc., to accept input instructions from the patient. In a practical application, the input can be provided by the performance capture system 708 to enable the patient to control the display of instruction video, the actions of performance capture system 708, and the real-time display of pose/motion captures via voice during the process of an exercise.

In some embodiments, a monitoring and assessment module 722 can employ computer vision and machine learning methods to monitor practice process, such as by matching the real pose/motion with the target pose/motion instructed by the care provider. In some embodiments, the monitoring and assessment module 722 can also or alternatively provide real-time feedback to the patient. As another example, the monitoring and assessment module 722 may provide graphic hints on a display screen to help the patient to adjust pose/motion. In yet further embodiments, the monitoring and assessment module 722 can also assess the progress of physical therapy according to the performance metrics defined by the care provider.

Server Management Subsystem

The server management subsystem 706 provides a centralized server to host databases and to provide high computational capabilities.

The server management subsystem 706 includes a server management engine 724 that facilitates connection to relevant databases, and to the patient digital twin information generated and updated by the platform 700. By way of example, a clinic and an individual patient connect to the centralized server, e.g., using an Azure cloud computer service. As such, clinics and individual patients can take various advantages provided by cloud computing at minimal cost and maximum convenience. In the example implementation illustrated, three databases are hosted by the server.

The physiotherapeutic scoliosis-specific exercise method database 714 (introduced briefly above), can be utilized to store various physiotherapeutic scoliosis-specific exercises. In a practical application, there are several schools of physiotherapeutic scoliosis-specific exercises methods. As an example, the Schroth physical therapy system can be included into the database. The Schroth physical therapy system is widely used in the United States and around the world. Schroth methods can be represented via 3-D modeling, e.g., in a 3D computer graphics software toolset, so that any physiotherapeutic scoliosis-specific exercises defined by the Schroth system can be easily mapped to the scoliosis patient digital twin of a particular patient.

A patient physical therapy database 726 can include various sets of data. By way of example, a patient physical therapy database 726 can include two sets of data. One set of data is the original scoliosis patient digital twin and its later versions which are updated periodically with new data of patient's body. These scoliosis patient digital twins together provide a detailed historical record of the changes of the body shape and musculoskeletal structure. The other set of data are the physiotherapeutic scoliosis-specific exercise training data. In an example implementation, the physiotherapeutic scoliosis-specific exercise training data are represented as 3-D games with the scoliosis patient digital twin used as an avatar.

A patient practice database 728 provides a real-time capture of a patient's physiotherapeutic scoliosis-specific exercises. The physiotherapeutic scoliosis-specific exercises can be recorded and kept in the database for a period of time. These records are used to track the progress of physical therapy and to assess the effectiveness of treatment.

The platform 700 can also incorporate a patient digital twin creation process 730. The patient digital twin creation process 730 can utilize template model techniques, fitting and morphing, and updating algorithms to generate and update a scoliosis patient digital twin. In an example embodiments, camera information from the performance capture system 708 can be combined with medical record data, e.g., from X-ray images 732. In this regard, the patient digital twin creation process 730 can utilize any techniques set out more fully herein, including the systems described with reference to FIG. 1 through FIG. 6 in any combination, to generate the digital twin virtualizations.

With reference to FIG. 7 generally, in an example practical application, the diagnosis and assessment module 710 performs observation, classification, pose/motion analysis and Cobb angle calculations. The diagnosis and assessment module 710 receives inputs from the performance capture system 708 and exchanges data with the physiotherapeutic scoliosis-specific exercise training and capture module 716. The diagnosis and assessment module 710 may further output information, e.g., scoliosis classification, Cobb angle, other data, etc. to the Clinical physiotherapeutic scoliosis-specific exercise management module 712.

In an example embodiment, the clinic physiotherapeutic scoliosis-specific exercise management module 712 performs selection, customization and planning. The clinic physiotherapeutic scoliosis-specific exercise management module 712 receives outputs from the patient digital twin creation module 730 and receives the outputs from the diagnosis and assessment module 710. Moreover, in some embodiments, the clinic physiotherapeutic scoliosis-specific exercise management module 712 outputs a physical therapy plan, physiotherapeutic scoliosis-specific exercise requirements, performance metrics, etc., to the physiotherapeutic scoliosis-specific exercise training and capture module 716 and to the patient database 726.

In an example embodiment, the physiotherapeutic scoliosis-specific exercise training and capture module 716 receives as inputs, the outputs from the clinic physiotherapeutic scoliosis-specific exercise management module 712. The physiotherapeutic scoliosis-specific exercise training and capture module 716 also receives inputs from the performance capture system 708 and the physiotherapeutic scoliosis-specific exercise training and capture module 716 exchanges data with the diagnosis and assessment module 710. The physiotherapeutic scoliosis-specific exercise training and capture module 716 can perform pose and motion demonstrations, generate games directed to instructing the patient in proper exercise and therapy, etc.

The physiotherapeutic scoliosis-specific exercise method database 714 receives inputs from the server management 724 and provides data to the clinic physiotherapeutic scoliosis-specific exercise management module 712.

The performance capture system 708 is any one or more device(s), software, combinations thereof, etc. that are generally referred to herein as measurement devices. Example devices include an image and/or video based system, which uses video and/or other sources of sensor data collection to provide patent measurements and recordings to the diagnosis and assessment module 710, to the patient digital twin creation process 730 (e.g., T-pose, multi-views, RGB-D images, etc.). The performance capture system 708 also provides data to the monitoring and assessment module 722.

The patient digital twin creation process 730 creates digital twins, e.g., using template model approaches, fitting and morphing, updating, etc., as set out more fully herein. The patient digital twin creation process 730 receives inputs from the performance capture system 708, from X-rays (or any other data, including data from the systems of FIG. 1, FIG. 2), or combinations thereof. The patient digital twin creation outputs patient digital twin information (e.g., patient digital twins, original data, updates, etc.) to the clinic PSSE management module 712 and to the PSSE practice and capture module 720.

The patient physical therapy database 726 receives inputs from the clinical PSSE management module 712, and the patient digital twin creation process 730, and provides data to the server management 724.

As noted more fully herein, in some embodiments, the server management 724 interacts with various databases, including the physiotherapeutic scoliosis-specific exercise method database 714, the patient physical therapy database 726, and the patient practice database 728.

In some embodiments, the patient physiotherapeutic scoliosis-specific exercise management module 718 handles planning, selection, composition, etc. Inputs are received form the patient physical therapy database. Moreover, the patient physiotherapeutic scoliosis-specific exercise management module 718 exchanges data with the monitoring and assessment module 722 (e.g., patient digital twin information, games, physiotherapeutic scoliosis-specific exercises, etc.). The patient physiotherapeutic scoliosis-specific exercise management module 718 may output visual instructions to a graphic display, and may output information to the physiotherapeutic scoliosis-specific exercise practice and capture module 720.

In some embodiments, the physiotherapeutic scoliosis-specific exercise practice and capture module 720 receives inputs in the from the performance and capture system 708, from the patient digital twin creation process 730 and from the monitoring and assessment module 722 (e.g., real-time captures, actual pose information, real-time feedback, interactions, etc.). The physiotherapeutic scoliosis-specific exercise practice and capture module 720 outputs information to the patient practice database.

The monitoring and assessment module 722 handles compliance, progress and feedback. The monitoring and assessment module 722 receives inputs from the patient physical therapy database 725, and from the performance capture system 708. The monitoring and assessment module 722 also exchanges data with the patient physiotherapeutic scoliosis-specific exercise management module 718. The monitoring and assessment module 722 outputs evaluation results and progress records to the patient practice database 728.

Other major tasks to be performed by the server management subsystem include user registration, clinic-patient communication, and privacy protection.

User Registration

In some embodiments, for clinic users, a two-step (password and verification code) can be used for login. For individual patients, the combination of password and the prescribed pose set with the performance capture system 708 can be used for login.

Clinic-Patient Communication

In an example implementation, there are two modes, offline and online. Offline communication will allow the care provider to track the progress of patient's physiotherapeutic scoliosis-specific exercises at home and to provide the feedback to the patient. Online communication enables telehealth, allowing the physical therapist to provide real-time instructions to the patient remotely. As a simplified example, communication can be facilitated via a video conferencing platform by sharing screen.

Privacy Protection

Scoliosis patient digital twin and physiotherapeutic scoliosis-specific exercises records contain personal information. Whereas personal data will be only shared with the clinic following the same rules applied to data sharing between a patient and doctor(s), additional technical measures, such as differential privacy, dimensionality reduction, and body masking may be implemented, if necessary, to protect the privacy of a patient.

Working Example 1—Physical Therapy Interfaces

In an example embodiment, a physical therapist uses the patient digital twin and a 3-D game for physiotherapeutic scoliosis-specific exercise design and patient education.

More specifically, the physical therapist logs onto the system. For instance, the physical therapist may be required to log in using a dual authentication protocol.

The physical therapist accesses a graphical user interface to access patient information of a patient having a patient digital twin from a patient database.

The graphical user interface graphically outputs a 3-D model of the patient on the display screen based upon the patent digital twin associated with the patient.

Using the graphical user interface, the physical therapist can perform preliminary assessments on the patient digital twin. As an example, the physical therapist can utilize the graphical user interface and patient digital twin to measure the Cobb angle and other indices.

In an example embodiment, the physical therapist can select a physiotherapeutic scoliosis-specific exercise from a database of exercises, e.g., as described more fully herein.

The physical therapist then uses the graphical user interface and a game generation algorithm on the platform to design and create a 3-D game to enable an individual to visualize the physiotherapeutic scoliosis-specific exercise on the patient digital twin.

The physical therapist can also utilize the game generation algorithm (or other means) to explain the exercise to a patient corresponding to the patient digital twin. The explanation can be recorded on the platform in text, video, audio, graphics, combinations thereof, etc.

In some example embodiments, the platform provides a patient interface as part of a graphical user interface. The patient can log into the platform, e.g., using dual authentication or other verification means as described more fully herein.

The patient can also utilize the graphical user interface to load exercise games, e.g., 3-D games generated by the physical therapist. In this regard, the patient can trigger a menu, command, or other feature of the user interface to receive electronic instructions in how to perform the exercise(s) associated with the 3-D game, as noted above.

In some embodiments, the user interface can also display a "cause and effect" of the exercise to the patient. The "cause and effect" provides an electronic feedback to a patient so that the patent understands the ramifications of the game/corresponding exercises.

Practically, the patient can log into a patient user interface from any location with network connectivity, including at a physical therapy office, at home, etc.

Working Example 2—Patient at Home Experience

As another working example, a patient can log into the platform from home, e.g., using a dual authentication or other verification protocol. In this regard, the patient can log into the platform using a web browser, app, proprietary application, etc.

Responsive to logging in, the platform can provide a graphical user interface that presents a set of menu options. An example menu option is an exercises menu option. By selecting the exercise option, the patient is permitted to select a physiotherapeutic scoliosis-specific exercise from a library of exercises, e.g., by selecting an exercise from a dropdown list of exercises.

Once the patient selects an appropriate exercise from the list of exercises, the graphical user interface automates a process to engage the patient in the selected exercise.

In an example embodiment, the user interface presents a graphical representation of an initial position/pose associated with the exercise. For instance, the graphical user interface can extract a corresponding patient from a patient database, e.g., by extracting a patient identifier. The patient identifier is used to load from a patient digital twin database, a specific patent digital twin that is uniquely associated with the patient. In this regard, the graphical user interface uses the extracted patient digital twin, e.g., which is graphically represented as a 3-D avatar, to demonstrate the initial pose position.

The patient mimics the pose/position demonstrated by the 3-D avatar of the patient digital twin. This starts the physiotherapeutic scoliosis-specific exercise.

In an example embodiment, the 3-D avatar adjusts the pose and muscle activation by demonstrating the correct exercise/pose/position on the graphical user interface. Moreover, the patient digital twin can provide instruction, coaching, feedback, audio cues, video cues, etc.

As an illustrative example, a camera, e.g., on the patient's laptop, smart phone, dedicated camera, etc., can be directed at the patient. Here, the camera functions as part of the performance capture system 708. The camera captures images (e.g., pictures, video or both) of the patient performing the physiotherapeutic scoliosis-specific exercise. The exercise application running on the platform extracts features from the captured images to track the patient's progress in the exercise, to identify when the patient is complete with the exercise, when the patient needs coaching, when the patient needs corrective instructions, etc.

The use of the exercise application allows the monitoring to occur in real-time, thus greatly reducing errors in performing exercises because deviations can be captured and identified immediately. Moreover, because the patient can observe the avatar/patient digital twin perform the exercise, the patient has a more relatable reference to understand the exercise, since the avatar will perform the exercise in a manner that mirrors how the patient is predicted to perform the exercise.

Once the exercise is complete, the exercise application can end the physiotherapeutic scoliosis-specific exercise. Upon completing the exercise, the exercise application presents to the patient, summary information including feedback so that the patient can understand how well the patient performed the exercise, how well the exercise is addressing the patient conditions, a trajectory to patient care milestones, etc.

The patient may select another exercise in a manner analogous to that described above, or the patient may exit the platform and log out.

Working Example—Replicate Physiotherapeutic Scoliosis-Specific Exercise

In a working example, a representation of a physiotherapeutic scoliosis-specific exercise is carried out via games, which is done at several different levels, e.g., three levels. The different levels enable different amounts of detail to be integrated into the games. A non-limiting set of example levels include:

- Generic level: a generic model (an avatar) of a healthy human is used to create games.
- Specific level: the specific model to represent each scoliosis type is used to create games.
- Individual level: the patient digital twin built for a particular patient is used to create games.

Based upon the above, an example of the individual level is described more fully. For instance, in an example embodiment, a patient performs a physiotherapeutic scoliosis-specific exercise in a clinic under the instruction by a physical therapist.

The platform captures the motion of the patient, e.g., using a performance capture system 708 described more fully herein. In this regard, the capture can be carried out using one or more cameras, sensors, scanners, combinations thereof, etc.

The platform creates a 3-D game that animates the patient digital twin (e.g., an avatar representing the patient digital twin) with the captured motion.

In some other embodiments, e.g., for the specific level or generic level, the patient need not be the source of the capture. However, capturing the patient performing the exercise in a clinical environment under the supervision of a physical therapist can result in an accurate representation of the exercise for the patient to practice at a later time, e.g., when not in the clinic/under supervision by the physical therapist.

Once the game is generated, the patient can log into the platform, e.g., using a patient portal as described more fully herein. Once in the portal, the patient can interact with a graphical user interface to select, play and replay the game to provide reference poses for a patient to practice the physiotherapeutic scoliosis-specific exercise, e.g., while performing therapy at home.

Working Example—Digital Twin Updating

In an example embodiment, a patient digital twin can contain various physical, physiological, and biological features and attributes, each of which needs to be updated in an appropriate time scale so that the digital twin can faithfully reflect the true states and status of its biological twin. The personal information from medical tests and examinations and personal data from wearable sensors are used to update those features and attributes.

Digital Twin Platform—General Purpose

The platform of FIG. 7 is illustrated in the context of scoliosis for purposes of clarity of discussion. However, the framework can be applied more generically, the digital twins of physical counterparts in other applications.

Figure 8:
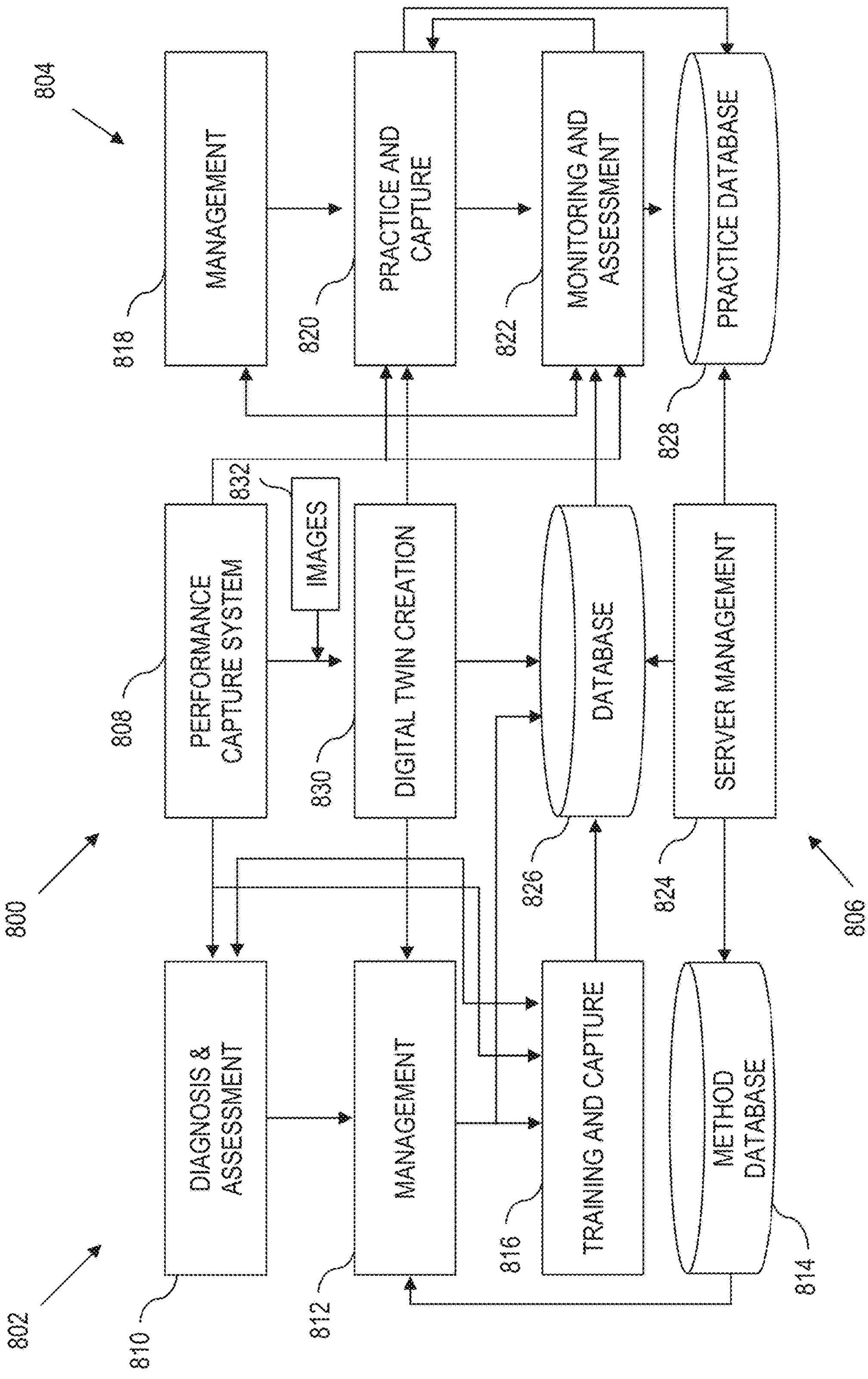
FIG. 8 is an example of a general framework with subsystems and databases according to aspects herein.

Referring to FIG. 8, an example is provided of a platform 800 for providing interactions with a digital twin. The platform 800 can be used to implement the platform 600, 700, etc., and thus the platform 800 can implement or otherwise utilize any combination of features described with reference to FIG. 1-FIG. 7. The platform 800 includes generally, three subsystems, including a clinical subsystem 802, a physical counterpart subsystem 804, and a management subsystem 806. The platform 800 also includes a performance capture system 808, which is analogous to the performance capture system 608 described with reference to FIG. 6 and/or the performance capture system 708 described with reference to FIG. 7.

Clinic Subsystem

The clinical subsystem 802 can provide a user interface to use the performance capture system 808. Moreover, the illustrated clinical subsystem 802 contains three modules, discussed below.

A diagnosis and assessment module 810 helps the platform user to make an accurate diagnosis and assessment decisions regarding a corresponding physical counterpart. The diagnosis and assessment module 810 provides functions for observation and classification of characteristics of the physical counterpart.

A management module 812 is utilized for selection, customization, and planning of interactions with physical counterparts to digital twins managed by the platform. In a practical application, the management module 812 includes user interface (UI) to make plans for interacting with the digital twins and/or physical counterparts.

The method database 814 stores data that defines specifications, e.g., for manipulating the digital twins and/or physical counterparts.

A training and capture module 816 provides demonstrations, and can optionally provide games that relate to testing the physical counterparts and/or digital twins.

Physical Counterpart Subsystem

The physical counterpart subsystem 804 enables remote evaluation and processing. A management module 818 generates a user interface with menu options that are navigable by an entity. The management module 818 also allows a use to select image/video and music to create a customized virtual environment.

A practice and capture module 820 can handle the input/output needs of the subsystem 804. For instance, in a practical application, the practice and capture module 820 can utilize at least one input device, e.g., a microphone, voice recognition capability, etc., to accept input instructions from the physical counterpart. In a practical application, the input can be provided by the performance capture system 808, and may be able to control the display of instruction video, the actions of performance capture system, and the real-time display of captures.

A monitoring and assessment module 822 can employ computer vision and machine learning methods to monitor practice process, such as by matching real pose/motion with a target pose/motion. In some embodiments, the monitoring and assessment module 822 can also or alternatively provide real-time feedback.

Server Management Subsystem

The server management subsystem 806 provides a centralized server to host databases and to provide high computational capabilities.

The server management subsystem 806 includes a server management engine 824 that facilitates connection to relevant databases, and to the patient digital twin information generated and updated by the platform 800.

The method database 814 can be utilized to store various specifications relevant to physical counterparts and/or digital twins.

A database 826 includes various sets of data regarding digital twins, and optionally, updates and histories thereto.

A practice database 828 provides a real-time capture of a physical counterpart interactions. Any such activities can be recorded and kept in the database for a period of time. These records are used to track progressions.

The platform 800 can also incorporate a digital twin creation process 830. The digital twin creation process 830 can utilize template model techniques, fitting and morphing, and updating algorithms to generate and update patient digital twin. In an example embodiments, camera information from the performance capture system 808 can be combined with other digital twin inputs. Moreover, the digital twin creation process 830 can be combined with any techniques set out more fully herein, including the systems described with reference to FIG. 1-FIG. 7 in any combination, to generate the digital twin virtualizations.

Example Digital Twin Creation Process

Figure 9:
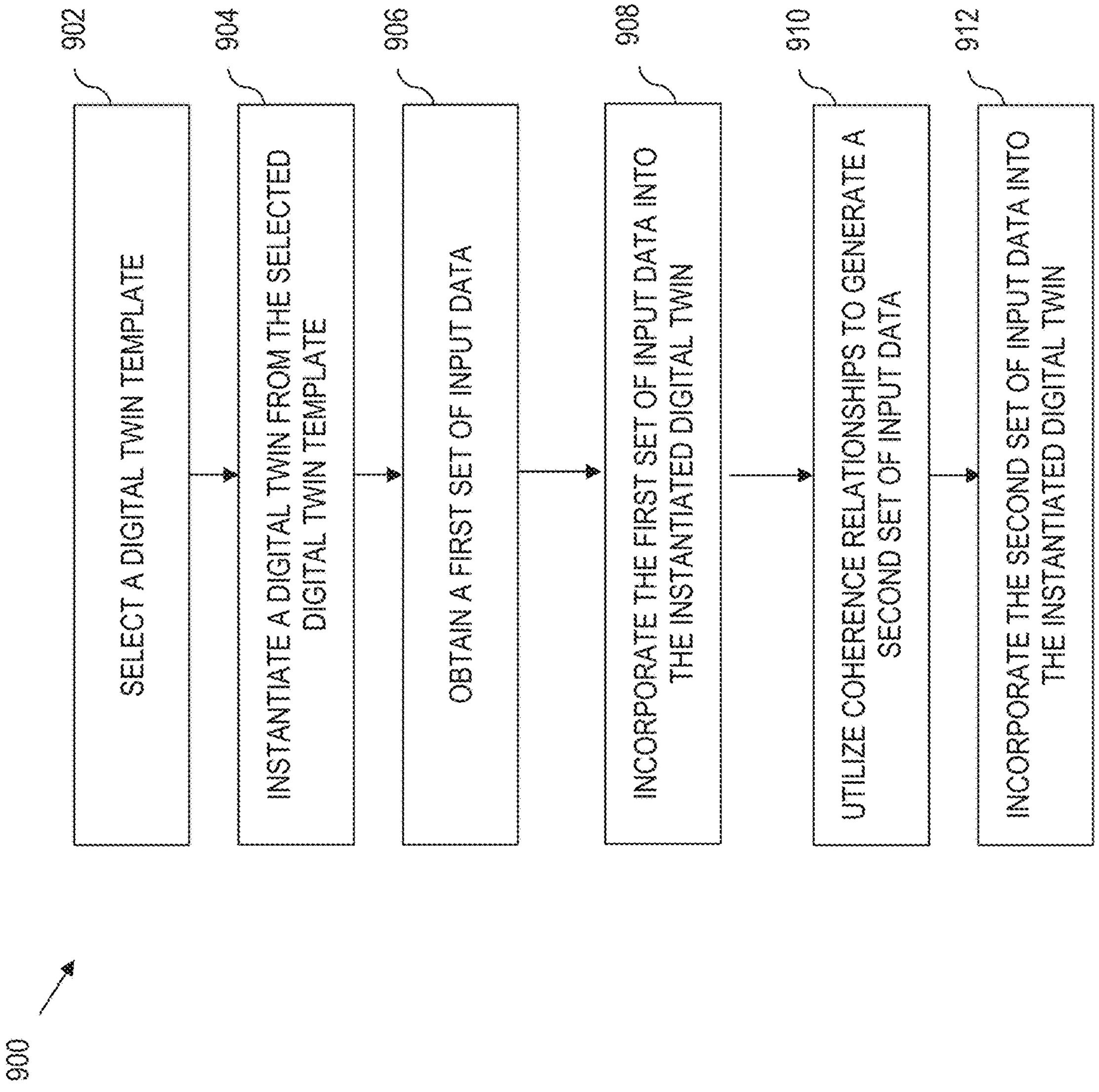
FIG. 9 is a flow chart illustrating a process for creating a digital twin according to aspects herein.

Referring to FIG. 9, an example digital twin creation process is illustrated. The process 900 can be implemented using any combination of features described more fully herein with reference to FIG. 1-FIG. 8 in any combination.

The process 900 comprises selecting at 902, a digital twin template. For instance, the selecting at 902 may comprise selecting a digital twin template that defines parameters that are in common with physical counterparts to be twinned using the selected digital twin template.

The process 900 also comprises instantiating at 904, a digital twin from the selected digital twin template.

The process 900 further comprises obtaining at 906, a first set of input data. For instance obtaining at 906 may comprise obtaining a first set of input data associated with a first set of parameters defined by the selected digital twin template, the first set of input data relating to a specific instance of a physical counterpart to be twinned.

The process 900 also includes incorporating at 908, the first set of input data into the instantiated digital twin.

The process 900 further comprises utilizing at 910, coherence relationships to generate a second set of input data. For instance, utilizing at 910 may comprise utilizing coherence relationships to generate a second set of input data, wherein the second set of input data comprises estimate values for a second set of parameters defined by the selected digital twin template, wherein the coherence relationships utilize the first set of input data to derive the second set of input data.

The process 900 also includes incorporating at 912, the second set of input data into the instantiated digital twin.

In some embodiments, the process 900 may comprise selecting the digital twin template comprises selecting a generic human template that includes anatomical parameters for a digital twin to represent characteristics of a counterpart human.

In some embodiments, the process 900 may comprise obtaining the preliminary set of data comprises collecting at least one measurement of a physical characteristic of the physical counterpart.

In some embodiments of the process 900, at least one measurement of a physical characteristic comprises a measurement of a length of an arm, a measurement of a length of a leg, a waist measurement, or a combination thereof.

In some embodiments, the process 900 may further comprise receiving input data about the physical counterpart that is twinned by the digital twin instance, using a data transfer mechanism to sort the received input data into input model data, storing the input model data in a model data storage, and extracting the input model data from the model data storage to update the instantiated digital twin instance. Moreover, in some embodiments, using the data transfer mechanism may further comprise manipulating the received input data into a format that matches at least one parameter of model data. Also, in some embodiments, selecting the digital twin template may comprise selecting the digital twin template associated with a human scoliosis patient, receiving input data about the physical counterpart that is twinned by the digital twin instance may comprise receiving input data from at least one wearable sensor worn by the physical counterpart that is twinned by the digital twin instance, and using the data transfer mechanism may comprise using the data transfer mechanism to sort the received input data from at least one wearable sensor into a data container. Yet further, in some embodiments, the process 900 also comprises utilizing unified physics-based digital human models combined with data-driven models and multiple data containers, at least one data container comprising the data container used to receive input data from the at least one wearable sensor, and at least one container receiving input from at least one of a medical record repository, an exercise repository and a medical image repository.

Example Process for Using a Digital Twin

Figure 10:
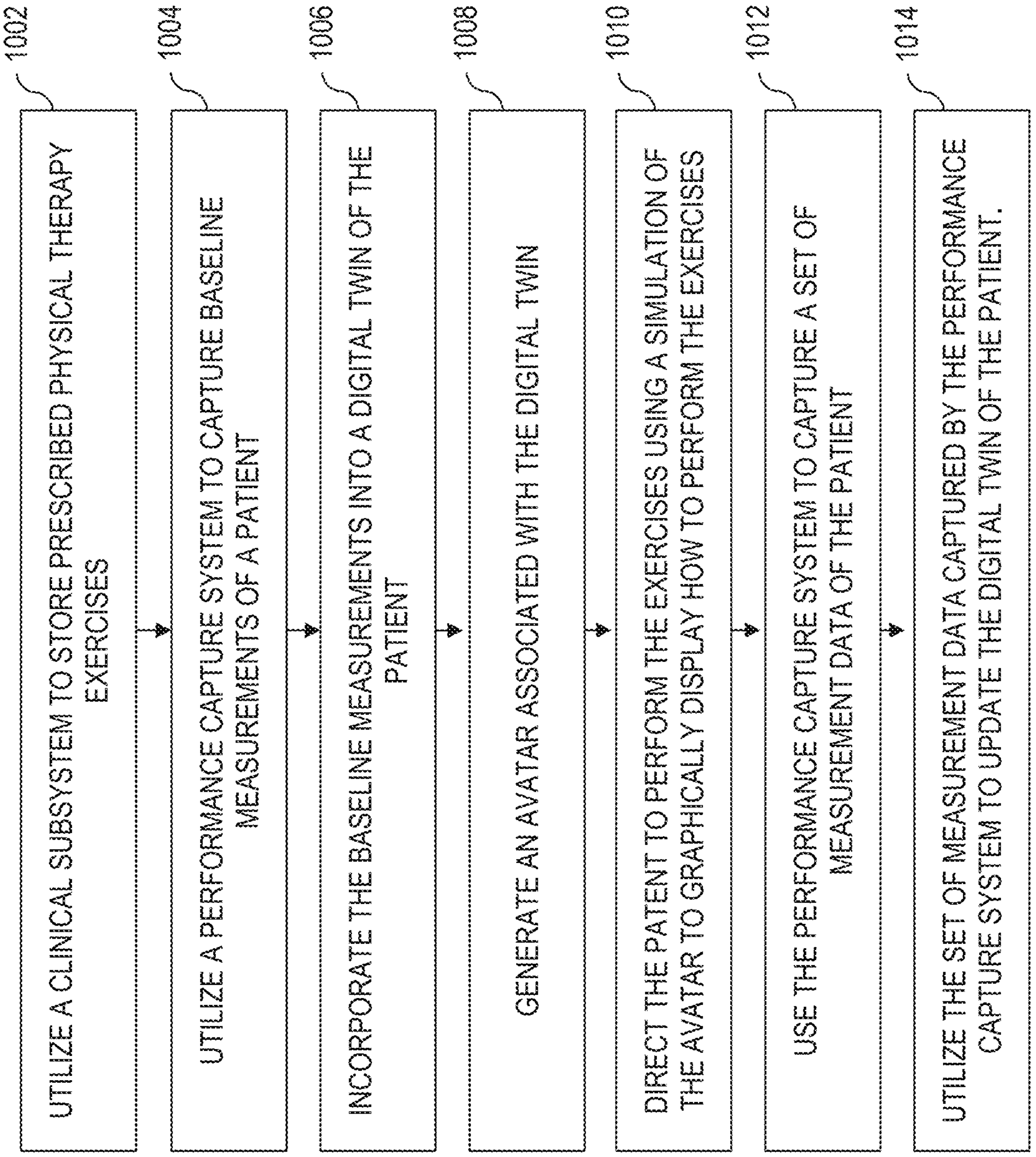
FIG. 10 is a flow chart illustrating a process for using a digital twin according to aspects herein.

Referring to FIG. 10, an example process of using a digital twin is illustrated. The process 1000 can be implemented using any combination of features described more fully herein with reference to FIG. 1-FIG. 9 in any combination.

The process 1000 comprises utilizing at 1002, a clinical subsystem to store prescribed physical therapy exercises. For instance, utilizing at 1002 may comprise utilizing a clinical subsystem to store in a computer platform, prescribed physical therapy exercises for a patient with scoliosis, wherein the patient performs exercises under supervised instruction.

The process 1000 also comprises utilizing at 1004, utilizing a performance capture system to capture baseline measurements of the patient. For instance, utilizing at 1004 may comprise utilizing a performance capture system to capture baseline measurements of the patient performing the exercises under the supervised instruction.

The process 1000 also comprises incorporating at 1006, the baseline measurements into a digital twin of the patient.

The process 1000 further comprises generating at 1008, an avatar associated with the digital twin.

The process 1000 also comprises directing, at 1010, directing the patient to perform the exercises. For instance, directing at 1010 may comprise directing the patient to perform the exercises using a simulation of the avatar to graphically display how to perform the exercises. As another example, directing at 1010 may comprise directing, using a patient subsystem of the computer platform, the patient to perform the exercises generated by the clinical patient subsystem, in an unsupervised manner, using a simulation of the avatar to graphically display on a graphical user interface, how to perform the exercises.

The process 1000 further comprises using at 1012, the performance capture system to capture a set of measurement data of the patient. For instance, using at 1012, may comprise using the performance capture system to capture a set of measurement data of the patient responsive to the patient performing at least one exercise using the patient subsystem.

The process 1000 yet further comprises utilizing at 1014, utilizing the set of measurement data captured by the performance capture system of the patient subsystem to update the digital twin of the patient.

In some embodiments, the process 1000 may be configured such that using the performance capture system to capture a set of measurement data comprises capturing video of the patient performing the exercises. In an example embodiment, the process 1000 further comprises comparing the baseline measurements to the set of measurement data captured by the performance capture system to generate a message comprised of a select one of a positive reinforcement, a negative reinforcement, or a coaching reinforcement, and outputting to a graphical user interface in real-time, the generated message to alter the patient's performance of the exercise.

Example Platform

As yet another illustrative example, a patient digital twin platform may comprise a clinical subsystem, a patient subsystem, a performance capture system, and a patient digital twin engine. In this example configuration, the clinical subsystem prescribes physical therapy exercises for a patient, the patient subsystem directs the patient to perform the exercises prescribed by the clinical patient subsystem, the performance capture system captures measurement data of the patient responsive to the patient performing at least one physical therapy exercise prescribed by the clinical subsystem, and the patient digital twin engine updates a digital twin of the patient based at least in part, upon the measurement data from the performance capture system.

In some embodiments, the example patient digital twin platform further comprises a patient digital twin process that utilizes medical information and at least one medical image of the patient to generate the digital twin. Here, the patient digital twin process further generates at least one avatar that represents the digital twin, and the avatar is used by the patient subsystem to demonstrate the exercises presented to the patient. In some embodiments of this configuration, the platform may further comprise a data collection management system, where the data collection management system is configured to collect information about the patient, and transfer the collected data into categories of relevance to the corresponding patient digital twin, where the data collected into the categories is used by the patient digital twin process to update the digital twin of the patient. Also, in some embodiments of this configuration, the categories of relevance of the data collection management system pertains to the patient's shape and muscular-skeleton makeup. Yet further, in some embodiments of this configuration, the collected information of the data collection management system comprises at least one of an X-ray and a body scan, an X-ray in the A-P plane, and an X-ray in a lateral plane.

In some embodiments of the example patient digital twin platform, the clinical subsystem generates an output comprising at least one of observations based upon the measurement data from the performance capture system, classifications based upon the measurement data from the performance capture system, pose and motion analysis data based upon the measurement data from the performance capture system, and Cobb angle analysis data based upon the measurement data from the performance capture system, where a clinical management process uses the generated output of the clinical subsystem to prepare a physical therapy plan and generate the physical therapy exercises prescribed by the clinical subsystem as physiotherapeutic scoliosis-specific exercises specific to the patient. In some embodiments of this configuration, the patient subsystem may receive inputs comprising at least one of measurement data collected by the performance capture system or information extracted from a patient physical therapy database, and the physiotherapeutic scoliosis-specific exercises specific to the patient generated by the clinical management process performs at least one of compliance or progress analysis of the patient based upon the received input, and outputs evaluation results to a patient practice database.

In some embodiments of the example patient digital twin platform, the measurement data collected by the performance capture system comprises at least one of image data or video data, and the patient subsystem collects measurement data generated by the performance capture system, measures at least one of pose or motion, and outputs at least one of real-time feedback of patient interactions with the platform, and real-time capture of an actual pose.

In some embodiments, the example patient digital twin platform may further comprise a management subsystem, where the management subsystem comprises a cloud-based server that manages at least one of a patient physical therapy database, a physiotherapeutic scoliosis-specific exercise database, and a patient practice database, where the patient subsystem accesses the management system using a graphical user interface that enables the patient to access the management subsystem from a clinical environment and a non-clinical environment.

In some embodiments, the example patient digital twin platform may further comprise generating the digital twin by collecting medical test results associated with the patient, collecting medical health records associated with the patient, and collecting data from at least one real-time activity tracker associated with the patient.

Computer System Overview

Figure 11:
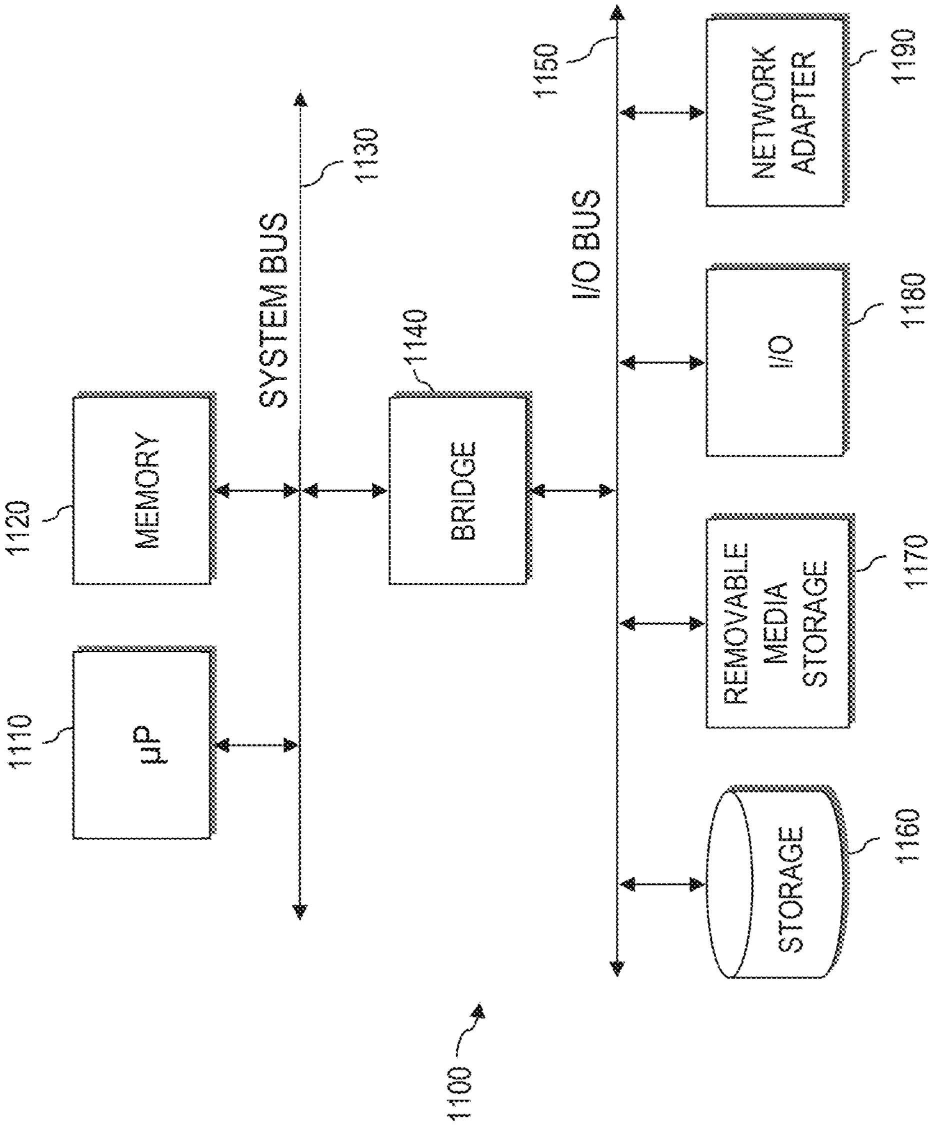
FIG. 11 is a block diagram of a computer processing system capable of implementing any of the systems or processes (or subsets thereof) described more fully herein.

Referring to FIG. 11, a schematic block diagram illustrates an exemplary computer system 1100 for implementing the various processes described herein. The exemplary computer system 1100 includes one or more (hardware) microprocessors (uP) 1110 and corresponding (hardware) memory 1120 (e.g., random access memory and/or read only memory) that are connected to a system bus 1130. Information can be passed between the system bus 1130 via a suitable bridge 1140 to a local bus 1150 that is used to communicate with various input/output devices. For instance, the local bus 1150 is used to interface peripherals with the one or more microprocessors (μP) 1110, such as storage 1160 (e.g., hard disk drives); removable media storage devices 1170 (e.g., flash drives, DVD-ROM drives, CD-ROM drives, floppy drives, etc.); I/O devices 1180 such as input device (e.g., mouse, keyboard, scanner, etc.), output devices (e.g., monitor, printer, etc.); and a network adapter 1190. The above list of peripherals is presented by way of illustration and is not intended to be limiting. Other peripheral devices may be suitably integrated into the computer system 1100.

The microprocessor(s) 1110 control operation of the exemplary computer system 800. Moreover, one or more of the microprocessor(s) 1110 execute computer readable code (e.g., stored in the memory 1120, storage 1160, removable media insertable into the removable media storage 1170 or combinations thereof, collectively or individually referred to as computer-program products) that instructs the microprocessor(s) 1110 to implement the computer-implemented processes herein.

The computer-implemented processes herein may be implemented as a machine-executable process executed on a computer system, e.g., one or more of the processes described more fully herein, in any of the preceding figures or combination thereof.

Thus, the exemplary computer system or components thereof can implement processes and/or computer-implemented processes stored on one or more computer-readable storage devices as set out in greater detail herein. Other computer configurations may also implement the processes and/or computer-implemented processes stored on one or more computer-readable storage devices as set out in greater detail herein. Computer-program code for carrying out operations for aspects of the present disclosure may be written in any combination of one or more programming languages. The program code may execute entirely on the computer system 1100 or partly on the computer system 1100. In the latter scenario, the remote computer may be connected to the computer system through any type of network connection, e.g., using the network adapter 1190 of the computer system 1100.

In implementing computer aspects of the present disclosure, any combination of computer-readable medium may be utilized. The computer-readable medium may be a computer readable signal medium, a computer-readable storage medium, or a combination thereof. Moreover, a computer-readable storage medium may be implemented in practice as one or more distinct mediums.

A computer-readable signal medium is a transitory propagating signal per se. A computer-readable signal medium may include computer readable program code embodied therein, for example, as a propagated data signal in baseband or as part of a carrier wave. More specifically, a computer-readable signal medium does not encompass a computer-readable storage medium.

A computer-readable storage medium is a tangible device/hardware that can retain and store a program (instructions) for use by or in connection with an instruction execution system, apparatus, or device, e.g., a computer or other processing device set out more fully herein. Notably, a computer-readable storage medium does not encompass a computer-readable signal medium. Thus, a computer readable storage medium, as used herein, is not to be construed as being transitory signals per se, such as radio waves or other freely propagating electromagnetic waves through a transmission media.

Specific examples (a non-exhaustive list) of the computer-readable storage medium include the following: a hard disk, a random-access memory (RAM), a read-only memory (ROM), an erasable programmable read-only memory (EPROM), Flash memory, a portable computer storage device, an optical storage device such as a compact disc read-only memory (CD-ROM) or digital video disk (DVD), or any suitable combination of the foregoing. In particular, a computer-readable storage medium includes computer-readable hardware such as a computer-readable storage device, e.g., memory. Here, a computer-readable storage device and computer-readable hardware are physical, tangible implementations that are non-transitory.

By non-transitory, it is meant that, unlike a transitory propagating signal per se, which will naturally cease to exist, the contents of the computer-readable storage device or computer-readable hardware that define the claimed subject matter persists until acted upon by an external action. For instance, program code loaded into random access memory (RAM) is deemed non-transitory in that the content will persist until acted upon, e.g., by removing power, by overwriting, deleting, modifying, etc.

Moreover, since hardware comprises physical element(s) or component(s) of a corresponding computer system, hardware does not encompass software, per se.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the invention in the form disclosed. Many modifications and variations will be apparent to those of ordinary skill in the art without departing from the scope and spirit of the disclosure.

Having thus described the invention of the present application in detail and by reference to embodiments thereof, it will be apparent that modifications and variations are possible without departing from the scope of the invention defined in the appended claims.

What is claimed is:

1. A patient digital twin platform, comprising:

a data collection management system, a clinical subsystem, a patient subsystem, a performance capture system, and a patient digital twin engine;

wherein:

the data collection management system is configured to collect data from an X-ray and a body scan and transfer the collected data into a corresponding patient digital twin generated by the patient digital twin engine;

the clinical subsystem is configured to generate and output a prepared physical therapy plan including physical therapy exercises specific to the patient based upon previously collected measurement data from the performance capture system;

the patient subsystem is configured to direct the patient to perform the physical therapy exercises prescribed by the clinical subsystem and output real-time feedback to the patient;

the performance capture system comprises at least one of a sensor or a camera and is configured to capture measurement data, including at least one of image data or video data of the patient, responsive to the patient performing at least one physical therapy exercise prescribed by the clinical subsystem; and the patient digital twin engine updates the digital twin of the patient based at least in part, upon the measurement data from the performance capture system.

2. The patient digital twin platform of claim 1 further comprising:

a patient digital twin process that utilizes medical information and at least one medical image of the patient to generate the patient digital twin;

wherein:

the patient digital twin process further generates at least one avatar that represents the patient digital twin; and the avatar is used by the patient subsystem to demonstrate the exercises presented to the patient.

3. The patient digital twin platform of claim 1 wherein:

the collected data is transferred into categories of relevance to the corresponding patient digital twin;

the data collected into the categories is used by the patient digital twin process to update the patient digital twin.

4. The patient digital twin platform of claim 3, wherein the categories of relevance of the data collection management system pertains to the patient's shape and muscular-skeleton makeup.

5. The patient digital twin platform of claim 3, wherein the collected information of the data collection management system comprises at least one of:

an X-ray and a body scan;

an X-ray in the A-P plane; and an X-ray in a lateral plane.

6. The patient digital twin platform of claim 1, wherein the output of the clinical subsystem comprising at least one of:

observations based upon the measurement data from the performance capture system;

classifications based upon the measurement data from the performance capture system;

pose and motion analysis data based upon the measurement data from the performance capture system; and Cobb angle analysis data based upon the measurement data from the performance capture system, wherein:

the generated output of the clinical subsystem includes physiotherapeutic scoliosis-specific exercises specific to the patient.

7. The patient digital twin platform of claim 6, wherein the patient subsystem:

receives inputs comprising at least one of:

measurement data collected by the performance capture system;

information extracted from a patient physical therapy database; and the physiotherapeutic scoliosis-specific exercises specific to the patient generated by the clinical management process;

performs at least one of compliance or progress analysis of the patient based upon the received input; and outputs evaluation results to a patient practice database.

8. The patient digital twin platform of claim 1, wherein:

the patient subsystem:

measures at least one of pose or motion; and outputs at least one of:

real-time feedback of patient interactions with the platform; and real-time capture of an actual pose.

9. The patient digital twin platform of claim 1 further comprising:

a management subsystem, the management subsystem comprising a cloud-based server that manages at least one of a patient physical therapy database, a physiotherapeutic scoliosis-specific exercise database, and a patient practice database;

wherein:

the patient subsystem accesses the management system using a graphical user interface that enables the patient to access the management subsystem from a clinical environment and a non-clinical environment.

10. The patient digital twin platform of claim 1 further comprising generating the digital twin by:

collecting medical test results associated with the patient;

collecting medical health records associated with the patient; and collecting data from at least one real-time activity tracker associated with the patient.

11. The patient digital twin platform of claim 1, wherein the patient digital twin engine is configured to create the digital twin, whereby the patient digital twin engine:

selects a digital twin template that defines parameters that are in common with the patient to be twinned using the selected digital twin template;

instantiates the digital twin from the selected digital twin template;

obtains a first set of input data associated with a first set of parameters defined by the selected digital twin template, the first set of input data relating to the patient to be twinned;

incorporates the first set of input data into the instantiated digital twin;

utilizes coherence relationships to generate a second set of input data, wherein the second set of input data comprises estimate values for a second set of parameters defined by the selected digital twin template, wherein the coherence relationships utilize the first set of input data to derive the second set of input data; and incorporates the second set of input data into the instantiated digital twin.

12. The patient digital twin platform of claim 11, wherein the digital twin template comprises a generic human template that includes anatomical parameters for a digital twin to represent characteristics of a counterpart human.

13. The patient digital twin platform of claim 12, wherein the preliminary set of data comprises at least one measurement of a physical characteristic of the physical counterpart.

14. The patient digital twin platform of claim 13, wherein the at least one measurement of a physical characteristic comprises a measurement of a length of an arm, a measurement of a length of a leg, a waist measurement, or a combination thereof.

15. The patient digital twin platform of claim 11, wherein the patient digital twin engine:

receives input data about the physical counterpart that is twinned by the digital twin instance;

uses a data transfer mechanism to sort the received input data into input model data;

stores the input model data in a model data storage; and extracts the input model data from the model data storage to update the instantiated digital twin instance.

16. The patient digital twin platform of claim 15, wherein the patient digital twin engine:

uses the data transfer mechanism further comprises manipulating the received input data into a format that matches at least one parameter of model data.

17. The patient digital twin platform of claim 15, wherein the patient digital twin engine:

selects the digital twin template comprises selecting the digital twin template associated with a human scoliosis patient;

receives input data about the physical counterpart that is twinned by the digital twin instance comprises receiving input data from at least one wearable sensor worn by the physical counterpart that is twinned by the digital twin instance; and uses the data transfer mechanism comprises using the data transfer mechanism to sort the received input data from at least one wearable sensor into a data container.

18. The patient digital twin platform of claim 17, wherein the patient digital twin engine:

utilizes unified physics-based digital human models combined with data-driven models and multiple data containers, at least one data container comprising the data container used to receive input data from the at least one wearable sensor, and at least one container receiving input from at least one of a medical record repository, an exercise repository and a medical image repository.

19. The patient digital twin platform of claim 1, wherein:

the clinical subsystem stores in a computer platform, prescribed physical therapy exercises for the patient, wherein the patient performs exercises under supervised instruction;

the performance capture system captures baseline measurements of the patient performing the exercises under the supervised instruction;

the patient digital twin engine incorporates the baseline measurements into the digital twin of the patient and generates an avatar associated with the digital twin;

the patient subsystem directs the patient to perform the exercises generated by the clinical patient subsystem, in an unsupervised manner, using a simulation of the avatar to graphically display on a graphical user interface, how to perform the exercises;

wherein:

the performance capture system captures a set of measurement data of the patient responsive to the patient performing at least one exercise using the patient subsystem; and the set of measurement data captured by the performance capture system of the patient subsystem are used to update the digital twin of the patient.

20. The patient digital twin platform of claim 19, wherein:

the performance capture system is used to capture a set of measurement data by capturing video of the patient performing the exercises;

the baseline measurements are compared to the set of measurement data captured by the performance capture system to generate a message comprised of a select one of a positive reinforcement, a negative reinforcement, or a coaching reinforcement; and a graphical user interface outputs in real-time, the generated message to alter the patient's performance of the exercise.

* * * * *